US006288228B1

(12) United States Patent
Henkin et al.

(10) Patent No.: US 6,288,228 B1
(45) Date of Patent: Sep. 11, 2001

(54) TRIAZINE ANGIOGENESIS INHIBITORS

(75) Inventors: Jack Henkin, Highlank Park; Donald J. Davidson, Gurnee; George S. Sheppard, Wilmette; Keith W. Woods, Libertyville; Richard W. McCroskey, Waukegan, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/680,383

(22) Filed: Oct. 5, 2000

Related U.S. Application Data

(63) Continuation of application No. 09/209,396, filed on Dec. 10, 1998, now Pat. No. 6,150,362.
(60) Provisional application No. 60/069,592, filed on Dec. 12, 1997.

(51) Int. Cl.[7] .................. C07D 251/70; A61K 31/53; A61P 35/04
(52) U.S. Cl. .................. 544/197; 544/198; 544/208; 544/209; 544/210; 514/245
(58) Field of Search .................. 544/197, 198, 544/208, 209, 210; 514/245

(56) References Cited

U.S. PATENT DOCUMENTS 4,554,275 * 11/1985 Sempuku et al. .................. 544/206

FOREIGN PATENT DOCUMENTS 0 563 386 * 9/1992 (EP) .

62292771 * 6/1986 (JP) .

OTHER PUBLICATIONS

Mackenzie et al. J. Chem. Soc. Perkin trans. 1 3, 295–8, 1972. CAPLUS abstract provided.*
Stevens et al. Eur. J. Med. Chem, Chim. Ther. 19940, 375–9, 1984.CAPLUS abstract provided.*
Schilt et al. Talanta 15(5) 475–8, 1968. CAPLUS abstract provided.*
Zhubanov et al. Vysokomol. Scedin. Ser B 28(3) 225–6, 1986.*

* cited by examiner

Primary Examiner—Mukund J. Shah
Assistant Examiner—Venkataraman Balasubramanian
(74) Attorney, Agent, or Firm—B. Gregory Donner; Gregory W. Steele

(57) ABSTRACT

Compounds having Formula I

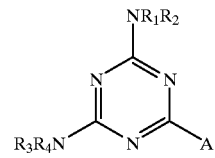

or pharmaceutically acceptable salts or prodrugs thereof, are useful for treating pathological states which arise from or are exacerbated by angiogenesis. The invention also relates to pharmaceutical compositions comprising these compounds and to methods of inhibiting angiogenesis in a mammal.

12 Claims, No Drawings

TRIAZINE ANGIOGENESIS INHIBITORS

This application is a continuation of U.S. Ser. No. 09/209,396, filed Dec. 10, 1998 now U.S. Pat. No. 6,150,362 which claims benefit of U.S. Provisional Application Ser. No. 60/069,592, filed Dec. 12, 1997.

TECHNICAL FIELD

The present invention relates to substituted triazines which are useful for treating pathological states which arise from or are exacerbated by angiogenesis, to pharmaceutical compositions comprising these compounds, and to methods of inhibiting angiogenesis in a mammal.

BACKGROUND OF THE INVENTION

Angiogenesis, the process by which new blood vessels are formed, is essential for normal body activities including reproduction, development and wound repair. Although the process is not completely understood, it is believed to involve a complex interplay of molecules which regulate the growth of endothelial cells (the primary cells of capillary blood vessels). Under normal conditions, these molecules appear to maintain the microvasculature in a quiescent state (i.e. one of no capillary growth) for prolonged periods which may last for as long as weeks or, in some cases, decades. When necessary (such as during wound repair), these same cells can undergo rapid proliferation and turnover within a 5 day period (Folkman, J. and Shing, Y., *The Journal of Biological Chemistry*, 267(16), 10931–10934, (1992) and Folkman, J. and Klagsbrun, M., *Science*, 235, 442–447 (1987).

Although angiogenesis is a highly regulated process under normal conditions, many diseases (characterized as angiogenic diseases) are driven by persistent unregulated angiogenesis. Otherwise stated, unregulated angiogenesis may either cause a particular disease directly or exacerbate an existing pathological condition. For example, ocular neovascularization has been implicated as the most common cause of blindness and dominates approximately twenty eye diseases. In certain existing conditions, such as arthritis, newly formed capillary blood vessels invade the joints and destroy cartilage. In diabetes, new capillaries formed in the retina invade the vitreous, bleed, and cause blindness. Growth and metastasis of solid tumors are also dependent on angiogenesis (Folkman, J., *Cancer Research*, 46, 467–473 (1986), Folkman, J., *Journal of the National Cancer Institute*, 82, 4–6 (1989). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone (Weidner, N., et al., *The New England Journal of Medicine*, 324(1), 1–8 (1991).

Several angiogenesis inhibitors are currently under development for use in treating angiogenic diseases (Gasparini, G. and Harris, A. L., *J. Clin. Oncol.*, 13(3): 765–782, 1995), but there are disadvantages associated with these compounds. Suramin, for example, is a potent angiogenesis inhibitor but causes severe systemic toxicity in humans at doses required for antitumor activity. Compounds such as retinoids, interferons and antiestrogens are relatively safe for human use but have weak antiangiogenic effects. Irsogladine, an anti-tumor drug with low toxicity, has only weak anti-angiogenic effects. Thus there is still a need for compounds useful in treating angiogenic diseases in mammals.

SUMMARY OF THE INVENTION

In one embodiment of the present invention are disclosed compounds having Formula I:

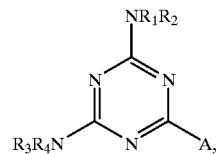

I or pharmaceutically acceptable salts or prodrugs thereof, wherein $R_1$, $R_2$, $R_3$, and $R_4$ are independently selected from the group consisting of hydrogen, $C_1$–$C_{20}$ alkyl, and $C_1$–$C_{20}$ alkanoyl; or $R_1$ and $R_2$ together with the nitrogen atom to which they are attached form a ring independently selected from the group consisting of morpholine, piperidine, piperazine, and pyrrolidine; or $R_3$ and $R_4$ together with the nitrogen atom to which they are attached form a ring independently selected from the group consisting of morpholine, piperidine, piperazine, and pyrrolidine;

A is selected from the group consisting of heterocycle, (heterocycle)-$C_1$–$C_{20}$-alkyl, $C_3$–$C_{10}$ cycloalkyl, $C_6$–$C_{15}$ spiroalkyl, and —B—L—Y;

B and Y are independently aryl, $C_3$–$C_{10}$ cycloalkyl, $C_4$–$C_{10}$ cycloalkenyl, heterocycle, or $C_6$–$C_{15}$ spiroalkyl;

L is a covalent bond, —C(=W)—, $C_1$–$C_{20}$ alkylene, —$NR_5$—, —$NR_6C(X)NR_7$—, $C_2$–$C_{20}$ alkynylene, $C_2$–$C_{20}$ alkenylene, —O—, —S(O)$_t$—, —$NR_6C(X)$—, —C(X)$NR_6$—, —$NR_6SO_2NR_7$—, —$NR_6SO_2$—, —$SO_2NR_6$—, or —O($CR_1R_2$)—;

$R_5$ is hydrogen, $C_1$–$C_{20}$ alkyl, $C_1$–$C_{20}$ alkanoyl, and $C_1$–$C_{20}$ arylalkyl;

$R_6$ and $R_7$ are independently hydrogen, $C_1$–$C_{20}$ alkyl, and aryl-$C_1$–$C_{20}$-alkyl;

$R_1$ and $R_2$ are previously defined;

W is O, S, or (=N—O—$R_6$);

X is O or S;

t is 0–2;

each L is shown with its left end attached to B and its right end attached to Y; and at each occurence, aryl, cycloalkyl, cycloalkenyl, heterocycle, spiroalkyl, alkylene, and (heterocycle)alkyl may be optionally substituted with 1–3 substituents independently selected from $C_1$–$C_{20}$ alkoxy, $C_1$–$C_{20}$ alkyl, amino, aryl, azido, cyano, halo, $C_1$–$C_{20}$ haloalkyl, heterocycle, nitro, or $R_{10}$ and $R_{11}$ wherein $R_{10}$ and $R_{11}$ together are

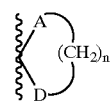

wherein A and D are independently oxygen or S(O)$_t$ and n is 2–3, with the proviso that when B and Y are unsubstituted phenyl and L is a covalent bond, then at least one of $R_1$, $R_2$, $R_3$, and $R_4$ is other than hydrogen, and with the proviso that when L is a covalent bond and one of B or Y is unsubstituted imidazole and the other is unsubstituted phenyl, then at least one of $R_1$, $R_2$, $R_3$, and $R_4$ is other than hydrogen.

In another embodiment of the invention are disclosed methods of treating diseases comprising administering an effective amount of a compound having Formula I.

In yet another embodiment of the invention are disclosed pharmaceutical compositions containing compounds of Formula I.

Compounds of this invention include, but are not limited to, a compound selected from the group consisting of:

6-[1-(diphenylmethyl)-3-azetidinyl]-1,3,5-triazine-2,4-diamine,
6-(1-phenyl-4-piperidinyl)-1,3,5-triazine-2,4-diamine,
trans-6-(4-phenylcyclohexyl)-1,3,5-triazine-2,4-diamine,
6-[3-(1H-pyrrol-1-yl)phenyl]-1,3,5-triazine-2,4-diamine,
cis/trans-6-(3-phenylcyclobutyl)-1,3,5-triazine-2,4-diamine,
6-[1,1'-biphenyl]-2-yl-1,3,5-triazine-2,4-diamine,
6-(4'-nitro[1,1'-biphenyl]-4-yl)-1,3,5-triazine-2,4-diamine,
6-[4-(4-pentylcyclohexyl)phenyl]-1,3,5-triazine-2,4-diamine,
6-(4-phenoxyphenyl)-1,3,5-triazine-2,4-diamine,
N-cyclohexyl-N'-[4-(4,6-diamino-1,3,5-triazin-2-yl)phenyl]urea,
(4,6-diamino-1,3,5-triazine-2-yl)phenylmethenone,
N-[4-(4,6-diamino-1,3,5-triazin-2-yl)phenyl]-N'-phenyl urea,
6-(1,4-dioxa-8-azaspiro[4,5]dec-8-yl)-1,3,5-triazine-2,4-diamine,
6-(4'-pentyl[1,1'-biphenyl]-4-yl)-1,3,5-triazine-2,4-diamine,
6-[4'-(pentyloxy)[1,1'-biphenyl]-4-yl]-1,3,5-triazine-2,4-diamine,
6-(6-methoxy-2-benzothiazolyl)-1,3,5-triazine-2,4-diamine,
6-(4'-amino[1,1'-biphenyl]-4-yl)-1,3,5-triazine-2,4-diamine,
6-[4-(5-oxazolyl)phenyl]-1,3,5-triazine-2,4-diamine,
6-[4-[[5-(trifluoromethyl)-2-pyridinyl]oxy]phenyl]-1,3,5-triazine-2,4-diamine,
4'-(4,6-diamino-1,3,5-triazine-2-yl)[1,1'-biphenyl]-4-carbonitrile,
6-(4'-methoxy[1,1'-biphenyl]-4-yl)-1,3,5-triazine-2,4-diamine,
6-(4'-fluoro[1,1'-biphenyl]-4-yl)-1,3,5-triazine-2,4-diamine
N-[4-(4,6-diamino-1,3,5-triazin-2-yl)phenyl]benzenesulfonamide,
6-[1-([1,1'-biphenyl]-4-yl)-4-piperidinyl]-1,3,5-triazine-2,4-diamine,
N-[4-(4,6-diamino-1,3,5-triazin-2-yl)phenyl]-2naphthalenesulfonamide,
2,5-dichloro-N-[4-(4,6-diamino-1,3,5-triazin-2-yl)phenyl]benzenesulfonamide,
6-(1-phenylcyclohexyl)-1,3,5-triazine-2,4-diamine,
6-[1-(4-methoxyphenyl)-4-piperidinyl]-1,3,5-triazine-2,4-diamine,
6-[2-[4-(trifluoromethyl)phenyl]-4-thiazolyl]-1,3,5-triazine-2,4-diamine,
6-[1-(4-methoxyphenyl)cyclohexyl]-1,3,5-triazine-2,4-diamine,
6-[4-(2-thienyl)phenyl]-1,3,5-triazine-2,4-diamine,
6-[4-(phenylethynyl)phenyl]-1,3,5-triazine-2,4-diamine,
N,N'-(6-[1,1'-biphenyl]-4-yl-1,3,5-triazin-2,4-diyl)bis[acetamide],
N-(4-amino-6-[1,1'-biphenyl]-4-yl-1,3,5-triazin-2-yl)acetamide,
N-[4-(4,6-diamino-1,3,5-triazin-2-yl)phenyl]-1-naphthalenesulfonamide,
6-(4'-azido[1,1'-biphenyl]-4-yl)-1,3,5-triazine-2,4-diamine,
6-[4-(4-morpholinylsulfonyl)phenyl]-1,3,5-triazine-2,4-diamine,
6-[4-(2-furanyl)phenyl]-1,3,5-triazine-2,4-diamine,
N,N'-[6-(4-phenoxyphenyl)-1,3,5-triazine-2,4-diyl]bis[acetamide],
N-[4-amino-6-(4-phenoxyphenyl)-1,3,5-triazin-2-yl]acetamide,
6-(5-phenyl-2-furanyl)-1,3,5-triazine-2,4-diamine,
6-(5-phenyl-2-thienyl)-1,3,5-triazine-2,4-diamine,
N,N'-[6-(4-phenylcyclohexyl)-1,3,5-triazin-2,4-diyl]bis[acetamide],
N-[4-amino-6-(4-phenylcyclohexyl)-1,3,5-triazin-2-yl]acetamide,
6-(4-phenyl-1-naphthalenyl)-1,3,5-triazine-2,4-diamine,
6-[4-(phenylthio)phenyl]-1,3,5-triazine-2,4-diamine,
6-(2-quinolinyl)-1,3,5-triazine-2,4-diamine,
6-(3-quinolinyl)-1,3,5-triazine-2,4-diamine,
6-(benzo[b]thien-2-ylmethyl)-1,3,5-triazine-2,4-diamine,
6-(2,2-dimethyl-2H-1-benzopyran-6-yl)-1,3,5-triazine-2,4-diamine,
6-(1-isoquinolinyl)-1,3,5-triazine-2,4-diamine
(6-(2,3-dihydro-1,4-benzodioxin-2-yl)-1,3,5-triazine-2,4-diamine,
6-(tricyclo[3.3.1.1$^{3,7}$]decan-1-yl)-1,3,5-triazine-2,4-diamine,
(+/-)-4-(4,6-diamino-1,3,5-triazine-2-yl)-α-phenylbenzenemethanol,
6-(2,3-dihydro-1,4-benzodioxin-6-yl)-1,3,5-triazine-2,4-diamine,
6-(1-azabicyclo[2.2.2]octan-4-yl)-1,3,5-triazine-2,4-diamine,
6-[4-(phenylsulfinyl)phenyl]1,3,5-triazine-2,4-diamine,
6-[4-(phenylsulfonyl)phenyl]-1,3,5-triazine-2,4-diamine,
[4-(4,6-diamino-1,3,5-triazine-2-yl)phenyl]phenylmethanone, oxime,
6-pyrazinyl-1,3,5-triazine-2,4-diamine,
2,4-diamino-6-[(4-phenylethenyl)phenyl]-1,3,5-triazine,
2,4-diamino-6-[(4-(2-nitrophenyl)ethenyl)phenyl]-1,3,5-triazine,
6-[1,1'-biphenyl]-4-yl-N,N'-dimethyl-1,3,5-triazine-2,4-diamine,
6-[1,1'-biphenyl]-4-yl-N-methyl-1,3,5-triazine-2,4-diamine,
6-(bicyclo[2.2.1]hept-2-yl)-1,3,5-triazine-2,4-diamine,
6-[1,1'-biphenyl]-4-yl-N,N'-diethyl-1,3,5-triazine-2,4-diamine,
6-(2'-nitro[1,1'-biphenyl]-4-yl)-1,3,5-triazine-2,4-diamine, 6-(6-methyl-3-pyridinyl)-1,3,5-triazine-2,4-diamine,
6-(6-chloro-3-pyridinyl)-1,3,5-triazine-2,4-diamine,
6-(5-bromo-3-pyridinyl)-1,3,5-triazine-2,4-diamine,
6-(2,3-dihydro-2,2,3,3-tetrafluoro-1,4-benzodioxin-6-yl)-1,3,5-triazine-2,4-diamine,
6-[4-[(4-chlorophenyl)methoxy]phenyl]-1,3,5-triazine-2,4-diamine,
6-[4-(1-piperidinylsulfonyl)phenyl]-1,3,5-triazine-2,4-diamine,
6-(1-benzoyl-4-piperidinyl)-1,3,5-triazine-2,4-diamine,
6-[1-(phenylmethyl)-4-piperidinyl]-1,3,5-triazine-2,4-diamine,
N,N'-diacetyl-6-[4-(phenylsulfonyl)phenyl]-1,3,5-triazine-2,4-diamine,
N-acetyl-6-[4-(phenylsulfonyl)phenyl]-1,3,5-triazine-2,4-diamine, and
6-(2-piperidin-1-ylphenyl)-1,3,5-triazine-2,4-diamine.

DETAILED DESCRIPTION OF THE INVENTION

Definition of Terms

The term "alkanoyl" as used herein represents an alkyl group of 1–20 carbon atoms attached to the parent molecular group through a carbonyl group.

The term "alkoxy" as used herein represents an alkyl group of 1–20 carbon atoms attached to the parent molecular group through an oxygen atom.

The term "alkyl" as used herein represents a monovalent group of 1–20 carbon atoms derived from a straight or branched chain saturated hydrocarbon. The alkyl groups of this invention may be substituted with 1–3 substituents independently selected from aryl or heterocycle.

The term "alkylene" as used herein represents a saturated divalent group of 1–20 carbon atoms derived from a straight or branched chain saturated hydrocarbon. The alkylene groups of this invention may be optionally substituted with oxo, thioxo, (=N—O—$R_6$), or —$OR_6$.

The term "alkenylene" as used herein represents an unsaturated divalent group of 2–20 carbon atoms derived from a straight or branched chain alkene.

The term "alkynylene" as used herein represents an unsaturated divalent group of 2–20 carbon atoms derived from a straight or branched chain alkyne.

The term "amino" as used herein represents —$NH_2$.

The term "aryl" as used herein represents a mono- or bicyclic carbocyclic ring system derived from one or two aromatic rings. The aryl groups of this invention may be optionally substituted with 1–4 substituents independently selected from alkoxy, alkyl, amino, aryl, azido, cyano, halo, haloalkyl, heterocycle, or nitro.

The term "arylalkyl" as used herein represents an aryl group attached to the parent molecular group through an alkyl group.

The term "azido" as used herein represents —$N_3$.

The term "cyano" as used herein represents —CN.

The term "cycloalkyl" as used herein represents a saturated monovalent group of 3–10 carbon atoms derived from a cyclic or bicyclic hydrocarbon. The cycloalkyl groups of this invention may be optionally substituted with 1–3 substituents independently selected from alkyl, aryl, or heterocycle.

The term "cycloalkenyl" as used herein represents an unsaturated monovalent group of 4–10 carbon atoms derived from a cyclic or bicyclic alkene. The cycloalkenyl groups of this invention may be optionally substituted with 1–3 substituents independently selected from alkyl, aryl, or heterocycle.

The term "halo" as used herein represents F, Cl, Br, or I.

The term "haloalkyl" as used herein represents an alkyl group to which is attached at least one halogen atom.

The term "heterocycle," as used herein, represents a 4-, 5-, 6-, or 7-membered ring containing one, two, or three heteroatoms independently selected from the group consisting of nitrogen, oxygen, and sulfur. The 4- and 5-membered rings have zero to two double bonds and the 6- and 7-membered rings have zero to three double bonds. These heterocycles include benzimidazolyl, benzofuranyl, benzothiazolyl, benzothienyl, benzoxazolyl, dihydrothienyl, dihydroindolyl, dihydrofuranyl, dihydropyranyl, dithiazolyl, furyl, homopiperidinyl, imidazolyl, imidazolinyl, imidazolidinyl, isothiazolyl, isothiazolidinyl, isoquinolinyl, indolyl, isoxazolyl, isoxazolidinyl, isothiazolyl, morpholinyl, oxazolidinyl, oxazolyl, piperazinyl, piperidinyl, pyranyl, pyrazinyl, pyrazolidinyl, pyrazolinyl, pyrazolyl, pyridyl, pyrrolidinyl, pyrrolinyl, pyrrolyl, pyridazinyl, pyrimidinyl, pyrimidyl, quinolinyl, tetrahydrofuranyl, tetrahydroisoquinolyl, tetrahydroquinolyl, tetrahydrothienyl, tetrazolyl, thiadiazolyl, thiazolidinyl, thiazolyl, thienyl, thiomorpholinyl, triazolyl, oxadiazolyl, and the like.

Heterocycles also includes bicyclic, tricyclic, and tetracyclic groups in which any of the aformentioned heterocyclic rings is fused to one or two rings independently selected from an aryl ring, a cyclohexane ring, a cyclohexene ring, a cyclopentane ring, a cyclopentene ring, or another monocyclic heterocyclic ring. These heterocycles include benzofuryl, benzothienyl, indolyl, isoquinolyl, quinolyl, tetrahydroquinolyl, and the like.

Heterocyclics also include compounds of the formula

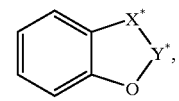

wherein X* is selected from —$CH_2$—, —$CH_2O$— and —O—, and Y* is selected from —C(O)— and —$(C(R")_2)_v$— wherein R" is hydrogen or alkyl of one to four carbon atoms and v is 1–3. These heterocycles include 1,3-benzodioxolyl, 1,4-benzodioxanyl, and the like. The heterocycles of this invention may be optionally substituted with 1–4 substituents independently selected from alkoxy, alkyl, amino, aryl, azido, cyano, halo, haloalkyl, heterocycle, nitro, or $R_{10}$ and $R_{11}$ wherein $R_{10}$ and $R_{11}$ together are

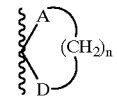

wherein A and D are independently oxygen or $S(O)_t$ and n is 2–3.

The term "(heterocycle)alkyl" as used herein represents an alkyl group substituted by a heterocycle. The (heterocycle)alkyl of this invention may be optionally substituted with aryl or heterocycle.

The term "hydroxy" as used herein represents —OH.

The term "nitro" as used herein represents —$NO_2$.

The term "oxo" as used herein represents (=O).

The term "pharmaceutically acceptable prodrugs" as used herein represents those prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "spiroalkyl" as used herein represents an alkylene diradical, both ends of which are bonded to the same carbon atom of the parent group to form a spirocyclic group. The spiroalkyl groups of this invention may be optionally substituted with 1–2 substituents independently selected from alkyl, aryl, or heterocycle.

The term "thioxo" as used herein represents (=S).

Asymmetric or chiral centers may exist in the compounds of the present invention. The present invention contemplates the various stereoisomers and mixtures thereof. Individual stereoisomers of compounds of the present invention are prepared synthetically from commercially available starting materials which contain asymmetric or chiral centers or by preparation of mixtures of enantiomeric compounds followed by resolution well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Pure enantiomers are designated herein by the symbols "R" or "S," depending on the configuration of subsitiuents around the chiral carbon atom.

Geometric isomers may also exist in the compounds of the present invention. The present invention contemplates the various geometric isomers and mixtures thereof resulting from the arrangement of substituents around a carbon-carbon double bond or arrangement of substituents around a carbocyclic ring. Substituents around a carbon-carbon double bond are designated as being in the Z or E configuration wherein the term "Z" represents substituents on the same side of the carbon-carbon double bond and the term "E" represents substituents on opposite sides of the carbon-carbon double bond. The arrangement of substituents around a carbocyclic ring are designated as cis or trans wherein the term "cis" represents substituents on the same side of the plane of the ring and the term "trans" represents substituents on opposite sides of the plane of the ring. Mixtures of compounds wherein the substitutients are disposed on both the same and opposite sides of plane of the ring are designated cis/trans.

Endothelial Cell Migration Assay

The endothelial cell migration assay was performed essentially as described by Polverini, P. J. et al., *Methods Enzymol*, 198: 440–450 (1991). Briefly, Human Microvascular Endothelial Cells (HMVEC) were starved overnight in DMEM (Dulbecco's Modified Eagle Medium) containing 0.1% bovine serum albumin (BSA). Cells were then harvested with trypsin and resuspended in DMEM with 0.1% BSA at a concentration of $1.5 \times 10^6$ cells/mL. Cells were added to the bottom of a 48-well modified Boyden chamber (Nucleopore Corporation, Cabin John, Md.). The chamber was assembled and inverted, and cells were allowed to attach for 2 hours at 37° C. to polycarbonate chemotaxis membranes (5 $\mu$m pore size) that had been soaked in 0.1% gelatin overnight and dried. The chamber was then reinverted and basic fibroblast growth factor (bFGF) and test substances were added to the wells of the upper chamber (to a total volume of 50 $\mu$L); the apparatus was then incubated for 4 hours at 37° C. Membranes were recovered, fixed and stained (DiffQuick, Fisher Scientific, Pittsburgh, Pa.) and the number of cells that had migrated to the upper chamber per 10 high power fields were counted. Background migration to DMEM+0.1% BSA was subtracted and the data reported as the number of cells migrated per 10 high power fields (400×) or when results from multiple experiments were combined, as the percent inhibition of migration compared to a positive control. The results are shown in Table 1.

TABLE 1

Inhibitory Potencies Against bFGF Induced Human Microvascular Endothelia Cell Migration of Representative Compounds

| Example | % inhibition at (nM) |
|---|---|
| Irsogladine | 53% (600 nM) |
| 1 | 20 (600) |
| 3 | 100 (600) |
| 4 | 62 (600) |
| 6 | 95 (600) |
| 7 | 100% (600 nM) |
| 8 | 30 (600) |
| 9 | 29 (600) |
| 10 | 29 (600) |
| 12 | 36 (600) |
| 13 | 53 (600) |
| 47 | 65 (600) |
| 48 | 55 (600) |
| 49 | 14 (600) |
| 50 | 100 (600) |
| 51 | 100 (600) |
| 52 | 100 (600) |
| 53 | 85 (600) |
| 55 | 84 (600) |
| 56 | 30 (600) |
| 58 | 100 (600) |
| 60 | 100 (600) |
| 63 | 79 (500) |
| 65 | 32 (200) |
| 68 | 73 (500) |
| 69 | 39 (500) |
| 74 | 82 (500) |
| 75 | 16 (500) |
| 76 | 33 (500) |
| 77 | 50 (500) |

The compounds of the invention, including but not limited to those specified in the examples, possess anti-angiogenic activity. As angiogenesis inhibitors, such compounds are useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas; prophylaxis of autoimmune diseases including rheumatoid, immune and degenerative arthritis; ocular diseases including diabetic retinopathy, retinopathy of prematurity, corneal graft rejection, retrolental fibroplasia, neovascular glaucoma, rubeosis, retinal neovascularization due to macular degeneration and hypoxia; abnormal neovascularization conditions of the eye; skin diseases including psoriasis; blood vessel diseases including hemagiomas and capillary proliferation within atherosclerotic plaques; Osler-Webber Syndrome; myocardial angiogenesis; plaque neovascularization; telangiectasia; hemophiliac joints; angiofibroma; wound granulation; diseases characterized by excessive or abnormal stimulation of endothelial cells including intestinal adhesions, Crohn's disease, atherosclerosis, scleroderma and hypertrophic scars (i.e. keloids) and diseases which have angiogenesis as a pathologic consequence including cat scratch disease (*Rochele minalia quintosa*) and ulcers (*Helicobacter pylori*). Another use is as a birth control agent which inhibits ovulation and establishment of the placenta.

The compounds of the present invention may also be useful for the prevention of metastases from the tumors described above either when used alone or in combination with radiotherapy and/or other chemotherapeutic treatments conventionally administered to patients for treating cancer. For example, when used in the treatment of solid tumors, compounds of the present invention may be administered with chemotherapeutic agents such as alpha intefeon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogs including methotrexate; pyrimidine analogues including 5-fluorouracil, cytosine arabinoside; purine analogs including 6-mercaptopurine and 6-thioguanine; antitumor antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar.

The compounds of the present invention may be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in *J. Pharmaceutical Sciences*, 1977, 66: 1 et seq. The salts may be prepared in situ during the final isolation and purification of the compounds of the invention or separately by reacting a free base function with a suitable acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quatemized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

Compounds of this invention may be combined with pharmaceutically acceptable sustained-release matrices, such as biodegradable polymers, to form therapeutic pocompositions. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix is desirably chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

Compounds of this invention or combinations thereof may be combined with pharmaceutically acceptable excipients or carriers to form therapeutic compositions. A pharmaceutically acceptable carrier or excipient refers to a non-toxic solid, semi-solid or liquid filler, diluent, encapsulating material or formulation auxiliary of any type. The compositions may be administered parenterally, sublingually, intracisternally, intravaginally, intraperitoneally, rectally, bucally or topically (as by powder, ointment, drops, transdermal patch or iontophoresis device).

The term "parenteral," as used herein, refers to modes of administration which include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

Topical administration includes administration to the skin, mucosa and surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers. For topical administration to the eye, a compound of the invention is delivered in a pharmaceutically acceptable ophthalmic vehicle such that the compound is maintained in contact with the ocular surface for a sufficient time period to allow the compound to penetrate the corneal and internal regions of the eye, as, for example, the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material. Alternatively, a compound of the invention may be injected directly into the vitreous and aqueous humor.

The composition may be pressurized and contain a compressed gas such as nitrogen or a liquified gas propellant. The liquified propellant medium and indeed the total composition is preferably such that the active ingredient does not dissolve therein to any substantial extent. The pressurized composition may also contain a surface active agent such as a liquid or solid non-ionic surface active agent or may be a solid anionic surface active agent. It is preferred to use the solid anionic surface active agent in the form of a sodium salt.

Compositions for rectal or vaginal administration are preferably suppositories which may be prepared by mixing the compounds of this invention with suitable non-irritating excipients or carriers such as cocoa butter, polyethylene glycol or a suppository wax which are solids at room temperature but liquids at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form may contain, in addition to a compound of the present invention, stabilizers, preservatives, excipients and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq., which is hereby incorporated herein by reference.

When used in the above or other treatments, a therapeutically effective amount of one of the compounds of the present invention may be employed in pure form or, where such forms exist, in pharmaceutically acceptable salt form and with or without a pharmaceutically acceptable excipient. A "therapeutically effective amount" of the compound of the invention means a sufficient amount of the compound to treat an angiogenic disease (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient;

the time of administration; the route of administration; the rate of excretion of the specific compound employed; the duration of the treatment; drugs used in combination or coincidental with the specific compound employed and like factors well known in the medical arts. For example, it is well within the skill of the art to start doses of the compound at levels lower than those required to achieve the desired therapeutic effect and to gradually increase the dosage until the desired effect is achieved. Total daily dose of compounds of this invention to be administered locally or systemically to a human or other mammal host in single or divided doses may be in amounts, for example, from 0.01 to 200 mg/kg body weight daily and more usually 1 to 300 mg/kg body weight. If desired, the effective daily dose may be divided into multiple doses for purposes of administration. Consequently, single dose compositions may contain such amounts or submultiples thereof to make up the daily dose.

It will be understood that agents which can be combined with the compound of the present invention for the inhibition, treatment or prophylaxis of angiogenic diseases are not limited to those listed above, but include, in principle, any agents useful for the treatment or prophylaxis of angiogenic diseases.

Preparation of Compounds of the Invention

Abbreviations

Abbreviations which have been used in the descriptions of the scheme and the examples that follow are: DMSO for dimethylsulfoxide, DME for dimethoxyethane, EtOAc for ethyl acetate, and THF for tetrahydrofuran.

Synthetic Methods

The compounds and processes of the present invention will be better understood in connection with the following synthetic schemes which illustrate the methods by which the compounds of the invention may be prepared.

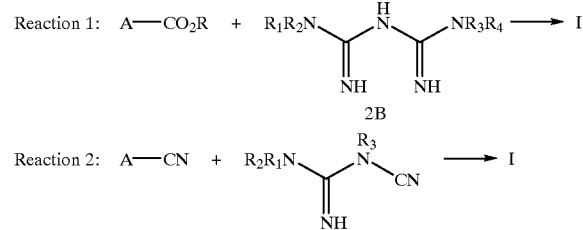

As shown in Scheme 1, the triazine ring of the compounds of Formula I were prepared from condensation of esters with biguanide (Reaction 1) or from condensation of nitriles and cyanoguanidine (Reaction 2). Reaction 2 was performed in a polar, high boiling solvent such as 2-methoxyethanol and in the presence of a strong base such as potassium hydroxide. Reaction 1 was performed in an an alcohol, preferably methanol. The ester and nitrile precursors were purchased from commercial sources or prepared using known chemical transformations.

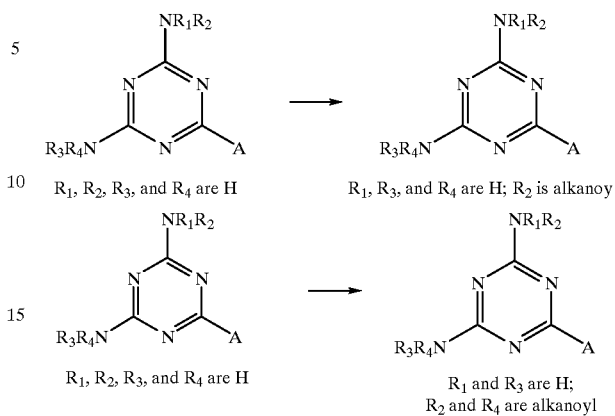

As shown in Scheme 2, selective mono acylation to provide compounds of Formula I was accomplished by heating a diaminotriazine precursor with a carboxylic acid anhydride at elevated temperature, preferably 80–90° C. Alternatively, 2,4-diacylation was accomplished by heating the diaminotriazine precursor with a carboxylic acid anhydride at higher temperatures, preferably 140–160° C.

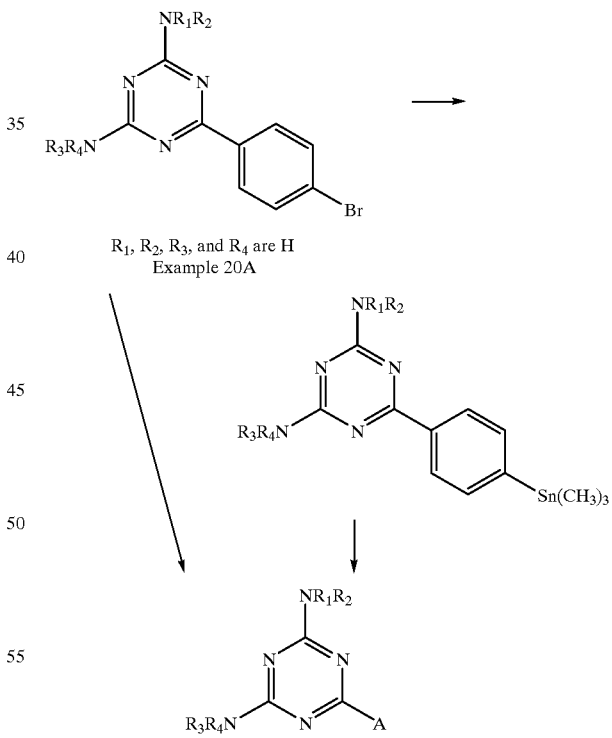

A is -B-L-Y; B and Y are optionally substituted aryl or heterocycle; and L is a covalent bond or alkynyl As shown in Scheme 3, 2,4-diamino-6-bromoaryl-triazines were converted to compounds of Formula I using transition metal-catalyzed cross-coupling reactions catalyzed by palladium catalysts such as tetrakis (triphenylphosphine) palladium. Also, conversion of Example 20A to a 2,4-diamino-6-(trialkylstannyl)aryl-triazine by treatment with organotin reagents, preferably hexamethylditin, in the presence of a palladium catalyst such as tetrakis(triphenylphosphine) palladium, followed by cross-coupling with aryl bromides, provided an alternative route to compounds of Formula I. Treatment of Example 20A with ethynyltin reagents such as trimethyl (phenylethylyl)tin in the presence of palladium catalysts such as tetrakis(triphenylphosphine) palladium also provided compounds of Formula I.

Scheme 4

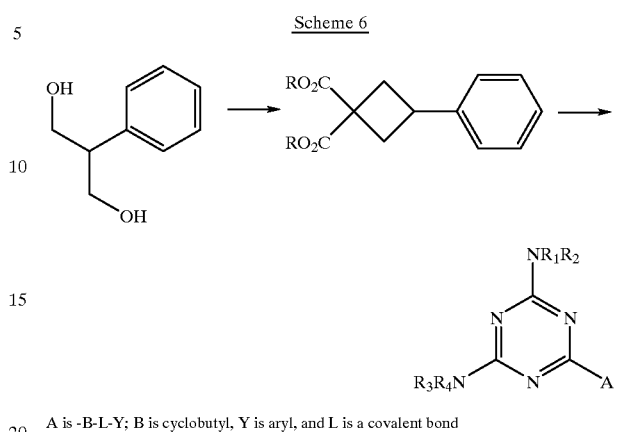

A is -B-L-Y, B is cyclohexyl, Y is optionally substituted aryl, and L is a covalent bond As shown in Scheme 4, compounds of Formula I were prepared by Friedel Crafts alkylation of aryl groups with a cycloalkenyl nitrile followed by elaboration of the nitrile intermediate as described in Scheme 1 (Reaction 2).

isonipecotic acid esters with triarylbismuth reagents in the presence of copper (II) acylates.

Scheme 6

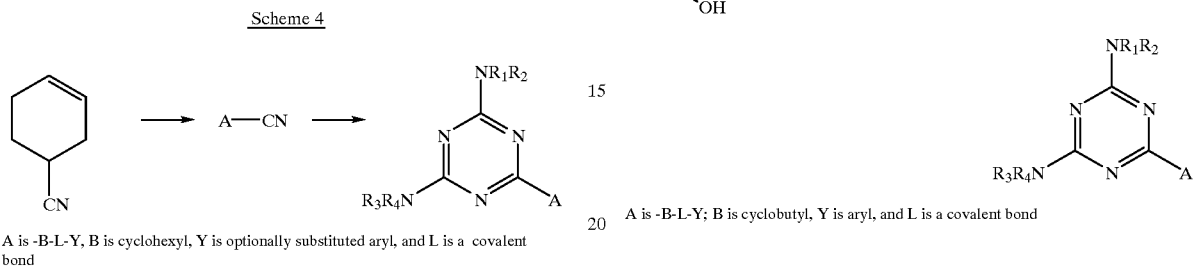

A is -B-L-Y; B is cyclobutyl, Y is aryl, and L is a covalent bond

As shown in Scheme 6, compounds of Formula I were prepared by condensation of bis-tosylates with malonic esters to construct cycloalkane rings, mono-decarboxylated at elevated temperatures, and further processed according to Scheme 1 (Reaction 1).

Scheme 7

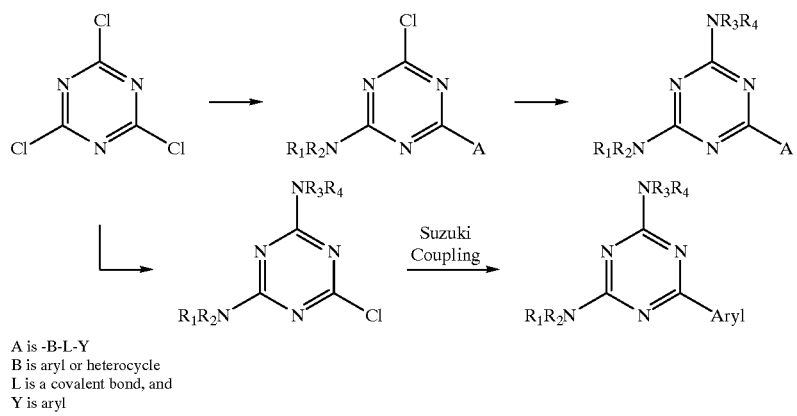

A is -B-L-Y
B is aryl or heterocycle
L is a covalent bond, and
Y is aryl

Scheme 5

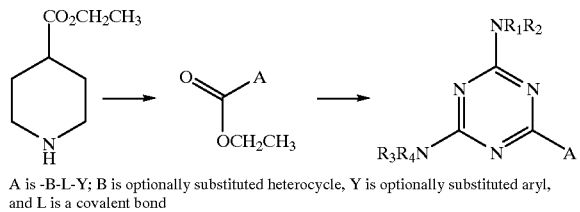

A is -B-L-Y; B is optionally substituted heterocycle, Y is optionally substituted aryl, and L is a covalent bond As shown in Scheme 5, piperidinyl aryl esters were converted to compounds of Formula I by arylation of As shown in Scheme 7, diaminotriazines bearing alkyl substituents on the amino groups can be prepared in a controlled and predicable manner by sequential displacement of chlorines from the triazine ring. The 6-aryl, heteroaryl, or cycloalkyl substituent may be introduced first by nucleophilic addition, for example as a Grignard reagent to cyanuric chloride, or after nitrogen introduction, for example by Pd-catalyzed Suzuki cross coupling with a boronic acid.

The compounds and processes of the present invention will be better understood in connection with the following examples, which are intended as an illustration of and not a limitation upon the scope of the invention.

EXAMPLE 1

6-[1-(diphenylmethyl)-3-azetidinyl]-1,3,5-triazine-2,4-diamine

A solution of 1-(diphenylmethyl)-3-azetidinecarbonitrile (500 mg, 2.01 mmol), dicyandiamide (220 mg, 2.62 mmol) and KOH (34 mg, 0.604 mmol) in 2-methoxyethanol (10 mL) was heated at reflux for 4 hours, diluted with water, and cooled to room temperature. The precipitate was rinsed with water and dried under vacuum to provide the title compound.

mp 126–128° C.; MS (DCI/NH$_3$) m/e 333 (M+H)$^+$; $^1$H NMR (300 MHz, DMSO-d$_6$) δ 7.3 (d, 4H), 7.2 (t, 4H), 7.05 (t, 2H), 6.5–6.7 (br s, 4H), 4.35 (s, 1H), 3.2–3.3 (m, 3H), 3.1–3.15 (m, 2H); Anal. calcd for $C_{19}H_{20}N_6 \cdot 0.75H_2O$: C, 65.97; H, 6.26; N, 24.29. Found: C, 65.67; H, 5.65; N, 23.84.

EXAMPLE 2

6-(1-phenyl-4-piperidinyl)-1,3,5-triazine-2,4-diamine

EXAMPLE 2A

A solution of triphenylbismuth (5.02 g, 11.4 mmol), cupric acetate (1.79 g, 9.85 mmol), and ethyl isonipecotate (1.5 mL, 9.7 mmol) in dichloromethane (100 mL) was stirred at room temperature for 18 hours, diluted with water, and filtered through Celite®. The organic layer was dried (MgSO$_4$), and concentrated. The residue was purified by flash chromatography on silica gel with 0–2% acetone/dichloromethane to provide the designated compound.

MS (DCI/NH$_3$) m/e 234 (M+H)$^+$.

EXAMPLE 2B

The designated compound was prepared as in Inorganic Synthesis, Volume 7, pp. 56–58 (1963).

EXAMPLE 2C 6-(1-Phenyl-4-piperidinyl)-1,3,5-triazine-2,4-diamine

A solution of Examples 2A (0.464 g, 1.99 mmol) and 2B (0.211 g, 2.09 mmol) in methanol (4 mL) was stirred at room temperature for 16 hours. The precipitate was rinsed with methanol, dried under vacuum, and recrystallized from dioxane/ethanol to provide the title compound.

mp 202–204° C.; MS (DCI/NH$_3$) m/e 271 (M+H)$^+$; $^1$H NMR (300 MHz, DMSO-d$_6$) δ 7.19 (t, 2H), 6.94 (d, 2H), 6.72 (t, 1H), 6.56 (br s, 4H), 4.11 (q, 2H), 3.77 (m, 2H), 2.75 (dt, 2H), 2.41 (m, 1H), 1.79 (m, 2H); Anal. calcd for $C_{14}H_{18}N_6 \cdot 0.67H_2O$: C, 59.58; H, 6.90; N, 27.78. Found: C, 59.27; H, 6.79; N, 25.51.

EXAMPLE 3 trans-6-(4-phenylcyclohexyl)-1,3,5-triazine-2,4-diamine

EXAMPLE 3A 4-phenylhexenecarbonitrile

A solution of cyclohexenecarbonitrile (9 mL, 80.6 mmol) and benzene (75 mL) was treated portionwise with AlCl$_3$ (13 g, 97 mmol) then stirred at room temperature for 2 hours. The mixture was poured onto ice and extracted with ethyl acetate. The extract was washed sequentially with water and brine, dried (MgSO$_4$), and concentrated. The residue was distilled at 125° C. (0.6 mm Hg) to provide the title compound.

MS (DCI/NH$_3$) m/e 203 (M+NH$_4$)$^+$.

EXAMPLE 3B trans-6-(4-phenylcyclohexyl)-1,3,5-triazine-2,4-diamine

Example 3A was processed as in Example 1 to provide the title compound.

MS (DCI/NH$_3$) m/e 270 (M+H)$^+$; $^1$H NMR (300 MHz, DMSO-d$_6$) δ 7.20–7.32 (m, 4H), 7.12–7.18 (m, 1H), 6.57 (br s, 4H), 2.46 (tt, 1H), 2.32 (tt, 1H), 1.80–1.93 (m, 4H), 1.41–1.66 (m, 4H); Anal. calcd for $C_{15}H_{19}N_5$: C, 66.88; H, 7.11; N, 26.00. Found: C, 66.85; H, 7.00; N, 26.08.

EXAMPLE 4

6-[3-(1H-pyrrol-1-yl)phenyl]-1,3,5-triazine-2,4-diamine 3-(1H-pyrrol-1-yl)benzonitrile was processed as in Example 1 to provide the title compound.

mp 164–170° C.; MS (DCI/NH$_3$) m/e 253 (M+H)$^+$; $^1$H NMR (300 MHz, DMSO-d$_6$) δ 8.35 (s, 1H), 8.15 (d, 1H), 7.7 (dd, 1H), 7.6–7.5 (m, 1H), 7.3 (t, 3H), 7.0–6.8 (br s, 4H), 6.3–6.25 (m, 2H); Anal. calcd for $C_{13}H_{12}N_6$: C, 61.89; H, 4.79; N, 33.31. Found: C, 62.20; H, 4.56; N, 32.39.

EXAMPLE 5 cis/trans-6-(3-phenylcyclobutyl)-1,3,5-triazine-2,4-diamine

A solution of cis/trans-methyl 3-phenylcyclobutane-1-carboxylate, prepared as in J. Am. Chem. Soc. 1985, 107, 7247–7257, was processed as in Example 2C to provide the title compounds.

mp 98–102° C.; $^1$H NMR (300 MHz, DMSO-d$_6$) δ 7.31 (m, 4H), 7.19 (m, 1H), 6.60 (m, 4H), 3.62 (m, 0.4H), 3.43 (m, 0.4H), 3.18 (m, 0.8H), 2.88 (m, 0.8H), 2.56 (m, 1.2H), 2.38 (m, 2.4H); Anal. calcd for $C_{13}H_{15}N_5 \cdot 0.5CH_3CO_2CH_2CH_3$: C, 63.14; H, 6.71; N, 24.54. Found: C, 62.75; H, 6.73; N, 24.48.

EXAMPLE 6

6-[1,1'-biphenyl]-2-yl-1,3,5-triazine-2,4-diamine

[1,1'-biphenyl]-2-carbonitrile was processed as in Example 1 to provide the title compound.

MS (DCI/NH$_3$) m/e 264 (M+H)$^+$; $^1$H NMR (300 MHz, DMSO-d$_6$) δ 7.63–7.2 (m, 5H), 7.37–7.27 (m, 4H), 6.6 (br s, 4H); Anal. calcd for $C_{15}H_{13}N_5$: C, 68.42; H, 4.97; N, 26.59. Found: C, 67.85; H, 4.94; N, 26.50.

EXAMPLE 7

6-(4'-nitro[1,1'-biphenyl]-4-yl)-1,3,5-triazine-2,4-diamine

4'-Nitro-[1,1'-biphenyl]-4-carbonitrile was processed as in Example 1 to provide the title compound.

mp>250° C.; MS (DCI/NH$_3$) m/e 309 (M+H)$^+$; $^1$H NMR (300 MHz, DMSO-d$_6$) δ 8.5–8.4 (m, 4H), 8.1 (d, 2H), 7.95 (d, 2H), 6.85 (br s, 4H); Anal. calcd for $C_{15}H_{12}N_6O_2$: C, 58.43; H, 3.92; N, 27.42. Found: C, 58.46; H, 3.76; N, 27.12.

EXAMPLE 8 trans-6-[4-(4-pentylcyclohexyl)phenyl]-1,3,5-triazine-2,4-diamine 4-(Trans-4-pentylcyclohexyl)benzonitrile was processed as in Example 1 to provide the title compound.

mp>250° C.; MS (DCI/NH$_3$) m/e 340 (M+H)$^+$; $^1$H NMR (300 MHz, DMSO-d$_6$) δ 8.2 (d, 2H), 7.3 (d, 2H), 6.75 (bs, 4H), 1.85 (d, 4H), 1.55–1.4 (m, 2H), 1.37–1.2 (m, 10H), 1.1–1.05 (m, 2H), 0.85 (t, 3H); Anal. calcd for C$_{20}$H$_{29}$N$_5$: C, 70.76; H, 8.61; N, 20.62. Found: C, 70.71; H, 8.73; N, 20.67.

EXAMPLE 9

6-(4-phenoxyphenyl)-1,3,5-triazine-2,4-diamine

4-Phenoxybenzonitrile was processed as in Example 1 to provide the title compound.

mp 198–200° C.; MS (DCI/NH$_3$) m/e 280 (M+H)$^+$; $^1$H NMR (300 MHz, DMSO-d$_6$) δ 8.3–8.2 (m, 2H), 7.5–7.4 (m, 2H), 7.2 (t, 1H), 7.17–7.0 (m, 4H), 6.9–6.65 (br s, 4H); Anal. calcd for C$_{15}$H$_{13}$N$_5$O: C, 64.51; H, 4.69; N, 25.07. Found: C, 63.84; H, 4.67; N, 24.90.

EXAMPLE 10

N-cyclohexyl-N'-[4-(4,6-diamino-1,3,5-triazin-2-yl)phenyl]urea

EXAMPLE 10A

4-Aminobenzonitrile was processed as in Example 1 to provide the designated compound.

MS (DCI/NH$_3$) m/e 203 (M+H)$^+$.

EXAMPLE 10B

N-cyclohexyl-N'-[4-(4,6-diamino-1,3,5-triazin-2-yl)phenyl]urea

A mixture of Example 10A (1.0 g; 4.9 mmol), cyclohexylisocyanate (610 mg, 4.9 mmol), and triethylamine (0.68 mL, 4.9 mmol) in dioxane was stirred overnight at room temperature. The precipitate was washed with water and dried under vacuum to provide the title compound.

MS (DCI/NH$_3$) m/e 328 (M+H)$^+$; $^1$H NMR (300 MHz, DMSO-d$_6$) δ 8.4 (s, 1H), 8.23 (t, 1H), 8.8–8.75 (m, 1H), 7.55–7.45 (m, 1H), 7.25–7.2 (t, 1H), 7.0–6.8 (br s, 4H), 6.0 (d, 1H), 3.55–3.4 (m, 1H), 1.9–1.8 (m, 2H), 1.7–1.6 (m, 2H), 1.59–1.5 (m, 1H), 1.2–0.5 (m, 5H); Anal. calcd for C$_{15}$H$_{21}$N$_7$O: C, 58.70; H, 6.47; N, 29.95. Found: C, 58.49; H, 6.59; N, 29.49.

EXAMPLE 11

(4,6-diamino-1,3,5-triazine-2-yl)phenylmethenone

4-Cyanobenzophenone was processed as in Example 1 to provide the title compound.

mp>250° C.; $^1$H NMR (300 MHz, DMSO-d$_6$) δ 8.4 (d, 2H), 7.9 (d, 2H), 7.8 (m, 2H), 7.7 (m, 1H), 7.6 (t, 2H), 6.9 (br s, 4H); MS (DCI/NH$_3$) m/e 292 (M+H)$^+$; Anal. calcd for C$_{16}$H$_{13}$N$_5$O: C, 65.97; H, 4.50; N, 24.04. Found: C, 65.74; H, 4.32; N, 23.93.

EXAMPLE 12

N-[4-(4,6-diamino-1,3,5-triazin-2-yl)phenyl]-N'-phenyl urea

Example 10A was processed as in Example 10B but substituting phenylisocyanate for cyclohexylisocyanate to provide the title compound.

$^1$H NMR (300 MHz, DMSO-d$_6$) δ 8.8 (s, 1H), 8.65 (s, 1H), 8.35 (t, 1H), 7.9 (d, 1H), 7.6–7.5 (m, 1H), 7.49–7.44 (m, 2H), 7.35 (t, 1H), 7.29 (t, 2H), 7.0 (t, 1H), 6.8–6.7 (br s, 4H); Anal. calcd for C$_{16}$H$_{15}$N$_7$O: C, 59.80; H, 4.70; N, 30.51. Found: C, 59.61; H, 4.72; N, 29.91.

EXAMPLE 13

6-(1,4-dioxa-8-azaspiro[4,5]dec-8-yl)-1,3,5-triazine-2,4-diamine

A mixture of 2,4-diamino-6-chloro-1,3,5-triazine (2 g, 14 mmol), 1,4-dioxa-8-azaspiro[4.5]decane (3 g, 21 mmol), and KOH (100 mg, 1.8 mmol) in dioxane (10 mL) and ethanol (40 mL) was heated at reflux overnight, diluted with water, and filtered. The precipitate was rinsed with water and dried under vacuum to provide the title compound.

mp 209–211° C.; MS (DCI/NH$_3$) m/e 253 (M+H)$^+$; $^1$H NMR (300 MHz, DMSO-d$_6$) δ 6.14 (br s, 4H), 3.90 (s, 4H), 3.75–3.68 (m, 4H), 1.58–1.51 (m, 4H); Anal. calcd for C$_{10}$H$_{16}$N$_6$O$_2$: C, 47.61; H, 6.39; N, 33.31. Found: C, 47.45; H, 6.34; N, 33.24.

EXAMPLE 14

6-(4'-pentyl[1,1'-biphenyl]-4-yl)-1,3,5-triazine-2,4-diamine

4'-Pentyl[1,1'-biphenyl]-4-carbonitrile was processed as in Example 1 to provide the title compound.

mp 242–244° C.; MS (DCI/NH$_3$) m/e 334 (M+H)$^+$; $^1$H NMR (300 MHz, DMSO-d$_6$) δ 8.3 (d, 2H), 8.75 (d, 2H), 8.65 (d, 2H), 7.3 (d, 2H), 6.75–6.82 (br s, 4H), 2.6 (t, 2H), 1.6–1.7 (m, 2H), 1.3–1.4 (m, 4H), 0.95 (t, 3H); Anal. calcd for C$_{20}$H$_{23}$N$_5$.0.25H$_2$O: C, 71.61; H, 7.09; N, 20.03. Found: C, 71.80; H, 7.00; N, 20.45.

EXAMPLE 15

6-[4'-pentyloxy[1,1'-biphenyl]-4-yl]-1,3,5-triazine-2,4-diamine

4'-(Pentyloxy)[1,1'-biphenyl]-4-carbonitrile was processed as in Example 1 to provide the title compound.

mp 246–249° C.; MS (DCI/NH$_3$) m/e 350 (M+H)$^+$; $^1$H NMR (300 MHz, DMSO-d$_6$) δ 8.3 (d, 2H), 7.75–7.65 (m, 4H), 7.07 (d, 2H), 6.85–6.7 (br s, 4H), 4.05 (t, 2H), 1.8–1.7 (m, 2H), 1.5–1.3 (m, 4H), 0.9 (t, 3H); Anal. calcd for C$_{20}$H$_{23}$N$_5$O: C, 68.75; H, 6.63; N, 20.04. Found: C, 68.64; H, 6.77; N, 19.94.

EXAMPLE 16

6-(6-methoxy-2-benzothiazolyl)-1,3,5-triazine-2,4-diamine

6-Methoxy-2-benzothiazolecarbonitrile was processed as in Example 1 to provide the title compound.

mp>250° C.; MS (DCI/NH$_3$) m/e 275 (M+H)$^+$; $^1$H NMR (300 MHz, DMSO-d$_6$) δ 7.98 (d, 1H), 7.71 (d, 1H), 7.17 (dd, 1H), 7.16 (br s, 2H), 6.95 (br s, 2H), 3.85 (s, 3H); Anal. calcd for C$_{11}$H$_{10}$N$_6$OS: C, 48.17; H, 3.67; N, 30.64. Found: C, 48.07; H, 3.75; N, 30.72.

EXAMPLE 17

6-(4'-amino[1,1'-biphenyl]-4-yl)-1,3,5-triazine-2,4-diamine

4'-Amino[1,1'-biphenyl]-4-carbonitrile was processed as in Example 1 to provide the title compound.

EXAMPLE 18

6-[4-(5-oxazolyl)phenyl]-1,3,5-triazine-2,4-diamine 4-(5-Oxazolyl)benzonitrile was processed as in Example 1 to provide the title compound.

MS (DCI/NH$_3$) m/e 255 (M+H)$^+$; $^1$H NMR (300 MHz, DMSO-d$_6$) δ 8.55 (s, 1H), 8.37 (d, 2H), 7.9–7.8 (t, 3H), 6.9–6.7 (br, s 4H); Anal. calcd for C$_{12}$H$_{10}$N$_6$O: C, 56.69; H, 3.96; N, 33.05. Found: C, 56.40; H, 4.02; N, 33.11.

EXAMPLE 19

6-[4-[[5-(trifluoromethyl)-2-pyridinyl]oxy]phenyl]-1,3,5-triazine-2,4-diamine

4-[[5-(Trifluoromethyl)-2-pyridinyl]oxy]benzonitrile was processed as in Example 1 to provide the title compound.

MS (DCI/NH$_3$) m/e 349 (M+H)$^+$; $^1$H NMR (300 MHz, DMSO-d$_6$) δ 8.6 (s, 1H), 8.6–8.5 (m, 3H), 7.4–7.3 (m, 3H), 6.9–6.7 (br s, 4H); Anal. calcd for C$_{15}$H$_{11}$F$_3$N$_6$O: C, 51.73; H, 3.18; N, 24.13. Found: C, 51.67; H, 3.20; N, 23.83.

EXAMPLE 20

4'-(4,6-diamino-1,3,5-triazine-2-yl)[1,1'-biphenyl]-4-carbonitrile

EXAMPLE 20A

4-Bromobenzonitrile was processed as in Example 1 to provide the designated compound.

MS (DCI/NH$_3$) m/e 267 (M+H)$^+$.

EXAMPLE 20B

A solution of Example 20A (0.76 g, 2.9 mmol) and tetrakis(triphenylphosphine) palladium (0.17 g, 0.15 mmol) in dry, degassed dimethylacetamide (45 mL) was heated to 100° C., treated with hexamethylditin (1.0 g, 3.1 mmol), heated at 100° C. for 3 hours, treated with ethyl acetate, washed sequentially with 1M NaOH and brine, dried (MgSO$_4$), and concentrated to provide the designated compound.

MS (DCI/NH$_3$) m/e 352 (M+H)$^+$.

EXAMPLE 20C

4'-(4,6-diamino-1,3,5-triazine-2-yl)[1,1'-biphenyl]-4-carbonitrile

A solution of Example 20B (0.95 g, 2.7 mmol), 4-bromobenzonitrile (0.55 g, 3.0 mmol) and tetrakis(triphenylphosphine) palladium (0.20 g, 0.17 mmol) in dry, degassed dimethylacetamide (45 mL) was heated at 100° C. for 3 hours, cooled to room temperature, treated with ethyl acetate, washed sequentially with 1M NaOH and brine, dried (MgSO$_4$), and concentrated. The residue was recrystallized from dioxane/ethanol to provide the title compound.

mp>260° C.; MS (DCI/NH$_3$) m/e 289 (M+H)$^+$; $^1$H NMR (300 MHz, DMSO-d$_6$) δ 8.36 (d, 2H), 7.96 (s, 4H), 7.88 (d, 2H), 6.81 (br s, 4H); Anal. calcd for C$_{16}$H$_{12}$N$_6$.0.75H$_2$O: C, 63.67; H, 4.51; N, 27.84. Found: C, 64.06; H, 4.38; N, 27.17.

EXAMPLE 21

6-(4'-methoxy[1,1'-biphenyl]-4-yl)-1,3,5-triazine-2,4-diamine

A solution of Example 20A (0.749 g, 2.8 mmol) and tetrakis(triphenylphosphine) palladium (0.15 g, 0.13 mmol) in dry, degassed dimethylacetamide (45 mL) was heated to 100° C., treated sequentially with 4-methoxyphenyl boronic acid (0.648 g, 4.3 mmol) in absolute ethanol (15 mL) and saturated NaHCO$_3$ (30 mL), heated at 100° C. for 3 hours, cooled to room temperature, treated with ethyl acetate, washed with brine, dried (MgSO$_4$), and concentrated. The residue was recrystallized from dioxane/ethanol to provide the title compound.

mp>260° C.; MS (DCI/NH$_3$) m/e 294 (M+H)$^+$; $^1$H NMR (300 MHz, DMSO-d$_6$) δ 8.31 (d, 2H), 7.72 (t, 4H), 7.03 (d, 2H), 6.86 (br s, 4H), 3.81 (s, 3H); Anal. calcd for C$_{16}$H$_{15}$N$_5$O.0.33H$_2$O: C, 64.21; H, 5.27; N, 23.40. Found: C, 64.26; H, 5.35; N, 23.43.

EXAMPLE 22

6-(4'-fluoro[1,1'-biphenyl]-4-yl)-1,3,5-triazine-2,4-diamine

Example 20A and 4-fluorophenyl boronic acid were processed as in Example 24 to provide the title compound.

mp>260° C.; MS (DCI/NH$_3$) m/e 282 (M+H)$^+$; $^1$H NMR (300 MHz, DMSO-d$_6$) δ 8.32 (d, 2H), 7.77 (m, 4H), 7.32 (t, 2H), 6.75 (br s, 4H); Anal. calcd for C$_{15}$H$_{12}$FN$_5$.0.25H$_2$O: C, 63.04; H, 4.41; N, 24.50. Found: C, 63.41; H, 4.49; N, 24.17.

EXAMPLE 23

N-[4-(4,6-diamino-1,3,5-triazin-2-yl)phenyl]benzenesulfonamide

A solution of Example 10A, (575 mg, 2.8 mmol) and benzenesulfonyl chloride (554 mg, 3.1 mmol) in pyridine (5 mL) was heated at reflux for 4 hours, stirred overnight at room temperature, treated with water and extracted with ethyl acetate. The extract was washed with water and brine, dried (MgSO$_4$), and concentrated. The residue was recrystallized from ethanol to provide the title compound.

mp 197–199° C.; MS (DCI/NH$_3$) m/e 343 (M+H)$^+$; $^1$H NMR (300 MHz, DMSO-d$_6$) δ 10.20 (br s, 1H), 8.03–8.01 (m, 1H), 7.94–7.91 (m, 1H); 7.80–7.78 (m, 2H), 7.60–7.50 (m, 3H), 7.34–7.25 (m, 1H), 7.22–7.19 (m, 1H); Anal. calcd for C$_{15}$H$_{14}$N$_6$O$_2$S.C$_2$H$_5$OH: C, 52.56; H, 5.18; N, 21.63. Found: C, 52.47; H, 5.24; N, 21.54.

EXAMPLE 24

6-[1-([1,1'-biphenyl]-4-yl)-4-piperidinyl]-1,3,5-triazine-2,4-diamine

EXAMPLE 24A

A mixture of 4-bromobiphenyl (19.16 g, 82 mmol) in THF (820 mL) at −78° C. was treated with tert-butyllithium (100 mL of a 1.7 M solution in pentane, 170 mmol), stirred for 8 minutes, treated with bismuth trichloride (8.62 g, 27.4 mmol) in THF (100 mL), stirred an additional 3 hours, treated with saturated aqueous NH$_4$Cl, and extracted with ethyl acetate. The extract was washed with water and brine, dried over (MgSO$_4$) and concentrated. The residue was dried in a vacuum oven to provide the designated compound.

$^{13}$C NMR (300 MHz, CDCl$_3$) δ 153.83, 141.04, 140.69, 138.07, 129.21, 128.75, 127.33, 127.07.

EXAMPLE 24B

6-[1-([1,1'-biphenyl]-4-yl)-4-piperidinyl]-1,3,5-triazine-2,4-diamine

Example 24A and ethyl isonipecotate were processed as in Examples 2A and 2C to provide the title compound.

mp>260° C.; MS (DCI/NH$_3$) m/e 347 (M+H)$^+$; $^1$H NMR (300 MHz, DMSO-d$_6$) δ 7.58 (m, 2H), 7.47 (d, 2H), 7.39 (m, 2H), 7.23 (m, 1H) 6.97 (d, 2H), 6.59 (br s, 4H), 3.61 (m, 1H), 1.78 (m, 4H), 1.58 (m, 4H).

EXAMPLE 25

N-[4-(4,6-diamino-1,3,5-triazin-2-yl)phenyl]-2-naphthalenesulfonamide 6-(4-Aminophenyl)-1,3,5-triazine-2,4-diamine was processed as in Example 23 but substituting 2-naphthalenesulfonyl chloride for benzenesulfonyl chloride to provide the title compound.

mp 230–233° C.; MS (DCI/NH$_3$) m/e 393 (M+H)$^+$; $^1$H NMR (300 MHz, DMSO-d$_6$) δ 10.55 (s, 1H), 8.5 (s, 1H), 8.2–8.05 (m, 3H), 8.0 (d, 1H), 7.9–7.85 (m, 1H), 7.8–7.75 (m, 1H), 7.74–7.6 (m, 2H), 7.3–7.2 (m, 2H), 6.9–6.65 (br s, 4H); Anal. calcd for C$_{19}$H$_{16}$N$_6$O$_2$S.1.5 C$_4$H$_8$O$_2$: C, 57.23; H, 5.37; N, 16.02. Found: C, 57.11; H, 5.33; N, 16.28.

EXAMPLE 26

2,5-dichloro-N-[4-(4,6-diamino-1,3,5-triazin-2-yl)phenyl]benzenesulfonamide

Example 10A was processed as in Example 23 but substituting 2,5-dichlorobenzenesulfonyl chloride for benzenesulfonyl chloride to provide the title compound.

mp 230–233° C.; MS (DCI/NH$_3$) m/e 411 (M+H)$^+$; $^1$H NMR (300 MHz, DMSO-d$_6$) δ 10.5 (s, 1H), 8.05 (m, 3H), 7.75–7.7 (m, 2H), 7.35 (t, 1H), 7.25–7.2 (m, 1H), 6.8–6.7 (br s, 4H); Anal. calcd for C$_{15}$H$_{12}$Cl$_2$N$_6$O$_2$S.0.5CH$_3$CH$_2$OH C, 44.24; H, 3.48; N, 19.35. Found: C, 44.43; H, 3.26; N, 19.44.

EXAMPLE 27

6-(1-phenylcyclohexyl)-1,3,5-triazine-2,4-diamine

1-Phenylcyclohexanecarbonitrile was processed as in Example 1 to provide the title compound.

mp 153–155° C.; MS (DCI/NH$_3$) m/e 270 (M+H)$^+$; $^1$H NMR (300 MHz, DMSO-d$_6$) δ 7.4–7.3 (m, 2H), 7.15 (t, 2H), 7.2–7.1 (m, 1H), 6.6–6.5 (br s, 4H), 2.7–2.6 (m, 2H), 1.75–1.6 (m, 2H), 1.6–1.2 (m, 6H); Anal. calcd for C$_{15}$H$_{19}$N$_5$: C, 66.89; H, 7.11; N, 26.00. Found: C, 66.94; H, 7.20; N, 26.04.

EXAMPLE 28

6-[1-(4-methoxyphenyl)-4-piperidinyl-1,3,5-triazine-2,4-diamine

Tris(4'-methoxy[1,1'-biphenyl]bismuth, prepared as in Example 24A, and ethyl isonipecotate were processed as in Examples 2A and 2C to provide the title compound.

mp 204–205° C.; MS (DCI/NH$_3$) m/e 301 (M+H)$^+$; $^1$H NMR (300 MHz, DMSO-d$_6$) δ 6.92 (d, 2H), 6.81 (d, 2H), 6.58 (m, 4H), 3.59 (m, 2H) 2.62 (m, 2H), 2.35 (m, 1H), 1.82 (m, 4H).

EXAMPLE 29

6-[2-[4-(trifluoromethyl)phenyl]-4-thiazolyl]-1,3,5-triazine-2,4-diamine

Ethyl 2-[4-(trifluoromethyl)phenyl]thiazole-4-carboxylate and Example 2B were processed as in Example 2C to provide the title compound.

mp>260° C.; MS (DCI/NH$_3$) m/e 339 (M+H)$^+$; $^1$H NMR (300 MHz, DMSO-d$_6$) δ 8.42 (s, 1H), 8.19 (d, 2H), 7.91 (d, 2H), 6.82 (br s, 4H); Anal. calcd for C$_{13}$H$_9$F$_3$N$_6$S: C, 46.15; H, 2.68; N, 24.84. Found: C, 45.85; H, 2.64; N, 24.44.

EXAMPLE 30

6-[1-(4-methoxyphenyl)cyclohexyl]-1,3,5-triazine-2,4-diamine 1-(4-Methoxyphenyl)cyclohexanecarbonitrile was processed as in Example 1 to provide the title compound.

mp 159–163° C.; MS (DCI/NH$_3$) m/e 300 (M+H)$^+$; $^1$H NMR (300 MHz, DMSO-d$_6$) δ 7.15 (d, 2H), 6.8 (d, 2H), 6.6 (br s, 4H), 3.7 (s, 3H), 2.7–2.6 (m, 2H), 1.7–1.6 (m, 2H), 1.6–1.2 (m, 6H); Anal. calcd for C$_{16}$H$_{21}$N$_5$O: C, 64.19; H, 7.07; N, 23.39. Found: C, 64.13; H, 7.07; N, 23.25.

EXAMPLE 31

6-[4-(2-thienyl)phenyl]-1,3,5-triazine-2,4-diamine

A solution of Example 20A (500 mg, 1.9 mmol) and 2-tri-n-butyltinthiophene (840 mg, 2.2 mmol) in dry, degassed dimethylacetamide (15 mL) was treated with tetrakis(triphenylphosphine) palladium (115 mg, 0.1 mmol), heated at 100° C. for 3 hours, cooled, treated with 1N NaOH, and extracted with ethyl acetate. The extract was washed with brine, dried (MgSO$_4$), and concentrated. The residue was recrystallized from ethanol/dioxane to provide the title compound.

mp>260; MS (DCI/NH$_3$) m/e 270 (M+H)$^+$; $^1$H NMR (300 MHz, DMSO-d$_6$) δ 8.31–8.24 (m, 2H), 7.8–7.72 (m, 2H), 7.62–7.59 (m, 2H), 7.2–7.16 (m, 1H), 6.92 (br s, 4H); Anal. calcd for C$_{13}$H$_{11}$N$_5$S: C, 57.97; H, 4.11; N, 26.00. Found: C, 57.91; H, 4.06; N, 25.83.

EXAMPLE 32

6-[4-(phenylethynyl)phenyl]-1,3,5-triazine-2,4-diamine

EXAMPLE 32A

4-Bromobenzonitrile and trimethyl(phenylethynyl)tin were processed as in Example 31 to provide the designated compound.

MS (DCI/NH$_3$) m/e 221 (M+NH$_4$)$^+$.

EXAMPLE 32B

6-[4-(phenylethynyl)phenyl]-1,3,5-triazine-2,4-diamine 4-(Phenylethynyl)benzonitrile was processed as in Example 1 to provide the title compound.

mp 248–249° C.; MS (DCI/NH$_3$) m/e 289 (M+H)$^+$; $^1$H NMR (300 MHz, DMSO-d$_6$) δ 8.30 (d, 2H), 7.67 (d, 2H), 7.61–7.58 (m, 2H), 7.5–7.43 (m, 3H), 6.82 (br s, 4H); Anal. calcd for C$_{17}$H$_{13}$N$_5$: C, 71.06; H, 4.56; N, 24.37. Found: C, 70.79; H, 4.73; N, 24.08.

EXAMPLE 33

N,N'-(6-[1,1'-biphenyl]-4-yl-1,3,5-triazin-2,4-diyl)bis[acetamide]

EXAMPLE 33A

4-Phenylbenzonitrile was processed as in Example 1 to provide the designated compound.

MS (DCI/NH$_3$) m/e 264 (M+H)$^+$.

EXAMPLE 33B

N,N'-(6-[1,1'-biphenyl]-4-yl-1,3,5-triazin-2,4-diyl) bis[acetamide]

A solution of Example 33A (0.26 g, 0.99 mmol) in acetic anhydride (10 mL) was refluxed for 20 hours and cooled to room temperature. The precipitate was rinsed with saturated $NaHCO_3$, and dried under vacuum to provide the title compound.

mp>260° C.; MS (DCI/$NH_3$) m/e 348 (M+H)$^+$; $^1$H NMR (300 MHz, DMSO-$d_6$) δ 10.79 (s, 2H), 8.43 (d, 2H), 7.91 (d, 2H), 7.79 (d, 2H), 7.52 (m, 2H), 7.41 (m, 1H), 2.41 (s, 6H); Anal. calcd for $C_{19}H_{17}N_5O_2$: C, 65.70; H, 4.93; N, 20.16. Found: C, 65.63; H, 4.84; N, 20.18.

EXAMPLE 34

N-(4-amino-6-[1,1'-biphenyl]-4-yl-1,3,5-triazin-2-yl) acetamide

A solution of Example 33A (0.38 g, 1.4 mmol) in acetic anhydride (4 mL) was heated at 80° C. for 20 hours, treated with ethyl acetate and cooled to room temperature. The precipitate was collected by vacuum filtration, rinsed with aqueous sodium carbonate, and dried under vacuum to yield the title compound.

mp>260° C.; MS (DCI/$NH_3$) m/e 306 (M+H)$^+$; $^1$H NMR (300 MHz, DMSO-$d_6$) δ 10.22 (s, 1H), 8.39 (d, 2H), 7.83 (d, 2H), 7.77 (d, 2H), 7.53 (m, 3H), 7.41 (m, 2H), 2.36 (s, 3H); Anal. calcd for $C_{17}H_{15}N_5O.0.2CH_3CO_2H$: C, 65.86; H, 5.02; N, 22.07. Found: C, 65.82; H, 4.97; N, 22.37.

EXAMPLE 35

N-[4-(4,6-diamino-1,3,5-triazin-2-yl)phenyl]-1-naphthalenesulfonamide

Example 10A was processed as in Example 23 but substituting 1-naphthalenesulfonyl chloride for benzenesulfonyl chloride to provide the title compound.

mp>250° C.; MS (DCI/$NH_3$) m/e 393 (M+H)$^+$; $^1$H NMR (300 MHz, DMSO-$d_6$) δ 10.8 (s, 1H), 8.8 (d, 1H), 8.3 (d, 1H), 8.2 (d, 1H), 8.1 (d, 1H), 8.0 (s, 1H), 7.83–7.6 (m, 4H), 7.2 (t, 1H), 7.15–7.1 (m, 1H), 6.83–6.7 (m, 4H); Anal. calcd for $C_{19}H_{16}N_6O_2S.H_2O$: C, 55.59; H, 4.42; N, 20.47. Found: C, 55.57; H, 4.42; N, 20.52.

EXAMPLE 36

6-(4'-azido[1,1'-biphenyl]-4-yl-1,3,5-triazine-2,4-diamine

EXAMPLE 36A

A solution of 4'-amino[1,1'-biphenyl]-4-carbonitrile (0.490 g, 2.53 mmol) in trifluoroacetic acid (12.5 mL) was treated sequentially with sodium nitrite (0.338 g, 4.90 mmol) and sodium azide (0.33 g, 5.1 mmol), stirred at room temperature for 10 minutes, treated with water and extracted with ethyl acetate. The extract was dried ($MgSO_4$), concentrated to provide the designated compound.

MS (DCI/$NH_3$) m/e 238 (M+$NH_4$)$^+$.

EXAMPLE 36B 6-(4'-azido-[1,1'-biphenyl]-4-yl)-1,3,5-triazine-2,4-diamine

Example 36A was processed as in Example 1 to provide the title compound.

mp 230° C. (decomposes); MS (DCI/$NH_3$) m/e 305 (M+H)$^+$; $^1$H NMR (300 MHz, DMSO-$d_6$) δ 8.32 (d, 2H), 7.79 (m, 4H), 7.24 (d, 2H), 6.74 (bds, 4H); Anal. calcd for $C_{15}H_{12}N_8.0.33H_2O$: C, 58.07; H, 4.11; N, 36.12. Found: C, 58.15; H, 3.84; N, 33.09.

EXAMPLE 37

6-[4-(4-morpholinylsulfonyl)phenyl]-1,3,5-triazine-2,4-diamine

EXAMPLE 37A

A solution of 4-cyanobenzenesulfonyl chloride (600 mg, 2.98 mmol), morpholine (300 mg, 3.44 mmol), and pyridine (350 μL, 342 mg, 4.33 mmol) in dichloromethane (10 ml) was stirred overnight at room temperature, treated with saturated $NH_4Cl$ and extracted with ethyl acetate. The extract was washed with water and brine, dried ($MgSO_4$) and concentrated to provide the designated compound.

MS (DCI/$NH_3$) m/e 270 (M+$NH_4$)$^+$.

EXAMPLE 37B 4-(2,4-diamino-1,3,5-triazin-2-yl)-N-(4-morpholinyl)benzenesulfonamide Example 37A was processed as in Example 1 to provide the title compound.

mp>260° C.; MS (DCI/$NH_3$) m/e 337 (M+H)$^+$; $^1$H NMR (300 MHz, DMSO-$d_6$) δ 8.46 (d, 2H), 7.83 (d, 2H), 6.91 (br s, 4H), 3.65–3.60 (m, 4H), 2.94–2.88 (m, 4H); Anal. calcd for $C_{13}H_{16}N_6O_3S$: C, 46.42; H, 4.79; N, 24.98. Found: C, 46.21; H, 4.69; N, 25.24.

EXAMPLE 38

6-[4-(2-furanyl)phenyl]-1,3,5-triazine-2,4-diamine 6-(4-Bromophenyl)-1,3,5-triazine-2,4-diamine was processed as in Example 31 but substituting 2-tri-n-butyltinfuran for 2-tri-n-butyltinthiophene to provide the title compound.

MS (DCI/$NH_3$) m/e 254 (M+H)$^+$; $^1$H NMR (300 MHz, DMSO-$d_6$) δ 8.3 (d, 2H), 7.8 (d, 3H), 7.05 (d, 1H), 6.8–6.7 (br s, 4H), 6.65–6.6 (m, 1H); Anal. calcd for $C_{13}H_{11}N_5O$: C, 60.30; H, 5.57; N, 24.30. Found: C, 59.83; H, 5.44; N, 24.86.

EXAMPLE 39

N,N'-[6-(4-phenoxyphenyl)-1,3,5-triazine-2,4-diyl] bis[acetamide]

Example 9 was processed as in Example 33B to provide the title compound.

mp 243–245° C.; MS (DCI/$NH_3$) m/e 364 (M+H)$^+$; $^1$H NMR (300 MHz, DMSO-$d_6$) δ 10.74 (s, 2H), 8.38 (d, 2H), 7.47 (t, 2H), 7.24 (t, 1H), 7.14 (dd, 4H), 2.38 (s, 6H); Anal. calcd for $C_{19}H_{17}N_5O_3$: C, 62.80; H, 4.72; N, 19.27. Found: C, 62.56; H, 4.82; N, 19.40.

EXAMPLE 40

N-[4-amino-6-(4-phenoxyphenyl)-1,3,5-triazin-2-yl] acetamide

Example 9 was processed as in Example 34 to provide the title compound.

mp>260° C.; MS (DCI/$NH_3$) m/e 322 (M+H)$^+$; $^1$H NMR (300 MHz, DMSO-$d_6$) δ 10.21 (s, 1H), 8.32 (d, 2H), 7.46 (t,

2H), 7.37 (bds, 2H), 7.13 (d, 2H), 7.08 (d, 2H), 2.32 (s, 3H); Anal. calcd for $C_{17}H_{15}N_5O_2$: C, 63.54; H, 4.71; N, 21.79. Found: C, 63.25; H, 4.79; N, 21.84.

EXAMPLE 41

6-(5-phenyl-2-furanyl)-1,3,5-triazine-2,4-diamine

EXAMPLE 41A

Methyl 5-bromo-2-furoate, phenylboronic acid, and tetrakis(triphenylphosphine) palladium were processed as in Example 21 to provide the designated compound.

MS (DCI/NH$_3$) m/e 203 (M+H)$^+$.

EXAMPLE 41B 6-(5-phenyl-2-furanyl)-1,3,5-triazine-2,4-diamine

Examples 41A and 2B were processed as in Example 2C to provide the title compound.

mp>260° C.; MS (DCI/NH$_3$) m/e 254 (M+H)$^+$; $^1$H NMR (300 MHz, DMSO-d$_6$) δ 7.80 (d, 2H), 7.52–7.44 (m, 2H), 7.41–7.37 (m, 1H), 7.23 (dd, 1H), 7.16 (dd, 1H), 6.78 (br s, 4H); Anal. calcd for $C_{13}H_{11}N_5O$: C, 61.65; H, 4.37; N, 27.65. Found: C, 61.33; H, 4.37; N, 27.42.

EXAMPLE 42

6-(5-phenyl-2-thienyl)-1,3,5-triazine-2,4-diamine

Methyl 5-phenylthiophene-2-carboxylate was processed as in Examples 41A and 41 B to provide the title compound.

mp>250° C.; MS (DCI/NH$_3$) m/e 270 (M+H)$^+$; $^1$H NMR (300 MHz, DMSO-d$_6$) δ 7.80 (d, 1H), 7.71–7.76 (m, 2H), 7.56 (d, 1H), 7.31–7.49 (m, 3H), 6.78 (bds, 4H); Anal. calcd for $C_{13}H_{11}N_5S.0.5H_2O$: C, 56.09; H, 4.34; N, 25.16. Found: C, 56.35; H, 4.01; N, 25.27.

EXAMPLE 43

N,N'-[6-(4-phenylcyclohexyl)-1,3,5-triazin-2,4-diyl]bis[acetamide]

Example 3 was processed as in Example 33B to provide the title compound.

mp 235–236° C.; MS (DCI/NH$_3$) m/e 354 (M+H)$^+$; $^1$H NMR (300 MHz, DMSO-d$_6$) δ 10.61 (s, 2H), 7.30 (m, 4H), 7.18 (m, 1H), 2.63 (m, 1H), 2.56 (m, 1H), 2.36 (s, 6H), 1.98 (m, 4H), 1.63 (m, 4H); Anal. calcd for $C_{19}H_{23}N_5O_2.0.25H_2O$: C, 63.76; H, 6.62; N, 19.57. Found: C, 63.83; H, 6.52; N, 19.27.

EXAMPLE 44

N-[4-amino-6-(4-phenylcyclohexyl)-1,3,5-triazin-2-yl]acetamide

Example 3 was processed as in Example 34 to provide the title compound.

mp>260° C.; MS (DCI/NH$_3$) m/e 312 (M+H)$^+$; $^1$H NMR (300 MHz, DMSO-d$_6$) δ 10.02 (s, 1H), 7.28 (m, 7H), 2.54 (m, 1H), 2.44 (m, 1H), 2.25 (s, 3H), 1.96 (m, 4H), 1.59 (m, 4H); Anal. calcd for $C_{17}H_{21}N_5O$: C, 65.57; H, 6.80; N, 22.49. Found: C, 65.37; H, 6.85; N, 22.74.

EXAMPLE 45

6-(4-phenyl-1-naphthalenyl)-1,3,5-triazine-2,4-diamine

EXAMPLE 45A

A solution of 4-methoxy-1-naphthalenecarbonitrile (3.5 g, 19 mmol) in dichloromethane (15 mL) at −78° C. was treated with BBr$_3$ (5 g, 20 mmol) in dichloromethane (15 mL), stirred at room temperature for 18 hours, treated with AlCl$_3$ (5 g, 38 mmol), stirred at room temperature for 18 hours, treated with water and extracted with ethyl acetate. The extract was washed with water and brine, dried (MgSO$_4$), and concentrated. The residue was purified by flash chromatography on silica gel with 30% ethyl acetate/hexane to provide the designated compound.

MS (DCI/NH$_3$) m/e 187 (M+NH$_4$)$^+$.

EXAMPLE 45B

A solution of Example 45A (1.0 g, 5.9 mmol), triethylamine (1 mL, 7.2 mmol) and N-phenyl-trifluoromethanesulfonamide (2.1 g, 5.9 mmol) in dichloromethane (15 mL) at 0° C. was stirred overnight at room temperature. The reaction was treated with ethyl acetate and washed sequentially with 10% HCl, 20% KOH, water, and brine, dried (MgSO$_4$), and concentrated to provide the designated compound.

MS (DCI/NH$_3$) m/e 319 (M+NH$_4$)$^+$.

EXAMPLE 45C

Example 45B and phenylboronic acid were processed as in Example 21 to provide the designated compound.

MS (DCI/NH$_3$) m/e 247 (M+NH$_4$)$^+$.

EXAMPLE 45D 6-(4-Phenyl-1-napthalenyl)-1,3,5-triazine-2,4-diamine

Example 45C was processed as in Example 1 to provide the title compound.

mp 239–240° C.; MS (DCI/NH$_3$) m/e 314 (M+H)$^+$; $^1$H NMR (300 MHz, DMSO-d$_6$) δ 8.84–8.80 (m, 1H), 7.97 (d, 1H), 7.85–7.81 (m, 1H), 7.69–7.48 (m, 8H), 6.84 (bds, 4H); Anal. calcd for $C_{19}H_{15}N_5$: C, 72.82; H, 4.82; N, 22.34. Found: C, 72.68; H, 4.77; N, 22.35.

EXAMPLE 46

6-[4-(phenylthio)phenyl]-1,3,5-triazine-2,4-diamine

EXAMPLE 46A

A solution of 4-bromobenzonitrile (1.0 g, 5.5 mmol), thiophenol (644 mg, 5.8 mmol), K$_2$CO$_3$ (1.9 g, 13.7 mmol) and CuI (1.05 g, 5.5 mmol) in DMF (20 mL) was heated at reflux for 24 hours, treated with ethyl acetate and filtered through Celite®. The filtrate was washed with water and brine, dried (MgSO$_4$), and concentrated. The residue was purified by flash chromatography on silica gel with 5% ethyl acetate/hexane to provide the designated compound.

MS (DCI/NH$_3$) m/e 229 (M+NH$_4$)$^+$.

EXAMPLE 46B

6-[4-(phenylthio)phenyl]-1,3,5-triazine-2,4-diamine

Example 46A was processed as in Example 1 to provide the title compound.

mp 213–215° C.; MS (DCI/NH$_3$) m/e 296 (M+H)$^+$; $^1$H NMR (300 MHz, DMSO-d$_6$) δ 8.19 (d, 2H), 7.44–7.41 (m, 5H), 7.32 (d, 2H), 6.77 (bds, 4H); Anal. calcd for $C_{15}H_{13}N_5S$: C, 60.99; H, 4.43; N, 23.71. Found: C, 60.70; H, 4.32; N, 23.55.

EXAMPLE 47

6-(2-quinolinyl)-1,3,5-triazine-2,4-diamine

2-Quinolinecarbonitrile was processed as in Example 1 to provide the title compound.

MS (DCI/NH$_3$) m/e 239 (M+H)$^+$; $^1$H NMR (300 MHz, DMSO-d$_6$) δ 8.5 (d, 1H), 8.35 (d, 1H), 8.15–8.0 (m, 2H), 7.9–7.8 (m, 1H), 7.75–7.7 (m, 1H), 7.1–7.0 (br s, 2H), 7.0–6.9 (br s, 2H); Anal. calcd for C$_{12}$H$_{10}$N$_6$: C, 60.49; H, 4.23; N, 35.27. Found: C, 60.24; H, 3.94; N, 35.12.

EXAMPLE 48

6-(3-quinolinyl)-1,3,5-triazine-2,4-diamine

3-Quinolinecarbonitrile was processed as in Example 1 to provide the title compound.

mp>250° C.; MS (DCI/NH$_3$) m/e 239 (M+H)$^+$; $^1$H NMR (300 MHz, DMSO-d$_6$) δ 9.7 (d, 1H), 9.1 (d, 1H), 8.2–8.1 (m, 2H), 6.9–6.85 (m, 1H), 6.8–6.7 (m, 1H), 7.05–6.9 (br s, 4H); Anal. calcd for C$_{12}$H$_{10}$N$_6$: C, 60.49; H, 4.23; N, 35.27. Found: C, 60.32; H, 4.06; N, 35.54.

EXAMPLE 49

6-(benzo[b]thien-2-ylmethyl)-1,3,5-triazine-2,4-diamine

Benzo[b]thiophene-2-acetonitrile was processed as in Example 1 to provide the title compound.

mp 216–218° C.; MS (DCI/NH$_3$) m/e 258 (M+H)$^+$; $^1$H NMR (300 MHz, DMSO-d$_6$) δ 7.97–7.92 (m, 1H), 7.87–7.80 (m, 1H), 7.48 (s, 1H), 7.4–7.32 (m, 2H), 6.65 (br s, 4H), 3.90 (s, 2H); Anal. calcd for C$_{12}$H$_{11}$N$_5$S: C, 56.01; H, 4.30; N, 27.21. Found: C, 55.97; H, 4.19; N, 27.31.

EXAMPLE 50

6-(2,2-dimethyl-2H-1-benzopyran-6-yl)-1,3,5-triazine-2,4-diamine 2,2-Dimethyl-2H-1-benzopyran-6-carbonitrile was processed as in Example 1 to provide the title compound.

MS (DCI/NH$_3$) m/e 270 (M+H)$^+$; $^1$H NMR (300 MHz, DMSO-d$_6$) δ 8.05 (dd, 1H), 7.95 (d, 1H), 6.9 (d, 1H), 6.78–6.75 (br s, 4H), 6.70 (d, 1H), 5.80 (d, 1H), 1.20 (s, 6H); Anal. calcd for C$_{14}$H$_{15}$N$_5$O: C, 62.44; H, 5.61; N, 26.00. Found: C, 62.19; H, 5.70; N, 25.54.

EXAMPLE 51

6-(2,3-dihydro-1,4-benzodioxin-2-yl)-1,3,5-triazine-2,4-diamine 2,3-Dihydro-1,4-benzodioxine-2-carbonitrile was processed as in Example 1 to provide the title compound.

MS (DCI/NH$_3$) m/e 246 (M+H)$^+$; $^1$H NMR (300 MHz, DMSO-d$_6$) δ 7.0–6.75 (m, 8H), 3.5 (t, 1H), 3.3 (d, 2H); Anal. calcd for C$_{11}$H$_{11}$N$_5$O$_2$: C, 53.81; H, 4.52; N, 28.55. Found: C, 53.80; H, 4.36; N, 28.40.

EXAMPLE 52

6-(tricyclo[3.3.1.1$^{3,7}$]decan-1-yl)-1,3,5-triazine-2,4-diamine

Methyl tricyclo[3.3.1.1$^{3,7}$]decane-1-carboxylate and Example 2B were processed as in Example 2C to provide the title compound.

mp 261–262° C.; MS (DCI/NH$_3$) m/e 246 (M+H)$^+$; $^1$H NMR (300 MHz, DMSO-d$_6$) δ 6.47 (br s, 4H), 2.05–1.95 (m, 3H), 1.9–1.88 (m, 6H), 1.77–1.60 (m, 6H); Anal. calcd for C$_{13}$H$_{19}$N$_5$: C, 63.64; H, 7.80; N, 28.54. Found: C, 63.48; H, 7.66; N, 28.34.

EXAMPLE 53

6-(1-isoquinolinyl)-1,3,5-triazine-2,4-diamine

1-Isoquinolinecarbonitrile was processed as in Example 1 to provide the title compound.

mp>250° C.; MS (DCI/NH$_3$) m/e 239 (M+H)$^+$; $^1$H NMR (300 MHz, DMSO-d$_6$) δ 8.7 (d, 1H), 8.2 (d, 1H), 8.0 (d, 1H), 7.9 (d, 1H), 7.8 (dt, 1H), 7.65 (dt, 1H), 6.9 (bs, 4H); Anal. calcd for C$_{12}$H$_{10}$N$_6$.0.3H$_2$O: C, 60.49; H, 4.23; N, 35.27. Found: C, 59.55; H, 4.35; N, 34.03.

EXAMPLE 54

(+/−)-4-(4,6-diamino-1,3,5-triazine-2-yl)-α-phenylbenzenemethanol

A mixture of Example 11 (150 mg, 0.515 mmol) and sodium borohydride (6 mg, 0.15 mmol) in ethanol (5 mL) was heated at reflux for 30 minutes then stirred overnight at room temperature. The precipitate was rinsed with water and dried under vacuum to provide the title compound.

mp 214–216° C.; MS (DCI/NH$_3$) m/e 294 (M+H)$^+$; $^1$H NMR (300 MHz, DMSO-d$_6$) δ 8.2 (d, 2H), 7.5 (d, 2H), 7.4 (d, 2H), 7.3 (t, 2H), 7.2 (m, 1H), 6.7 (br s, 4H), 6.0 (d, 1H), 5.75 (d, 1H); Anal. calcd for C$_{16}$H$_{15}$N$_5$O: C, 65.51; H, 5.15; N, 23.87. Found: C, 65.33; H, 4.91; N, 23.65.

EXAMPLE 55

6-(2,3-dihydro-1,4-benzodioxin-6-yl)-1,3,5-triazine-2,4-diamine 2,3-Dihydro-1,4-benzodioxine-6-carbonitrile was processed as in Example 1 to provide the title compound.

mp 241–244° C.; MS (DCI/NH$_3$) m/e 246 (M+H)$^+$; $^1$H NMR (300 MHz, DMSO-d$_6$) δ 8.8–8.75 (m, 2H), 6.95–6.9 (m, 1H), 6.9–6.8 (br s, 4H), 4.25–4.33 (m, 4H); Anal. calcd for C$_{11}$H$_{11}$N$_5$O$_2$: C, 53.87; H, 4.52; N, 28.56. Found: C, 53.93; H, 4.27; N, 28.41.

EXAMPLE 56

6-(1-azabicyclo[2.2.2]octan-4-yl)-1,3,5-triazine-2,4-diamine

1-Azabicyclo[2.2.2]octane-4-carbonitrile was processed as in Example 1 to provide the title compound.

mp>245° C.; MS (DCI/NH$_3$) m/e 221 (M+H)$^+$; $^1$H NMR (300 MHz, DMSO-d$_6$) δ 6.6–6.5 (br s, 4H), 3.35 (s, 2H), 2.9 (t, 5H), 1.7 (t, 5H); Anal. calcd for C$_{10}$H$_{16}$N$_6$: C, 54.53; H, 7.32; N, 38.15. Found: C, 54.40; H, 7.38; N, 38.25.

EXAMPLE 57

6-[4-(phenylsulfinyl)phenyl]1,3,5-triazine-2,4-diamine

A mixture of Example 49 (102 mg, 0.34 mmol) and Oxone® (106 mg, 0.17 mmol) in acetic acid (2 mL) was stirred overnight at ambient temperature, treated with saturated NaHCO$_3$ and extracted with ethyl acetate. The extract was washed with water and brine, dried (MgSO$_4$), and concentrated. The residue was recrystallized from ethanol to provide the title compound.

mp 253–255° C.; MS (DCI/NH$_3$) m/e 312 (M+H)$^+$; $^1$H NMR (300 MHz, DMSO-d$_6$) δ 8.36 (d, 2H), 7.81 (d, 2H), 7.75–7.72 (m, 2H), 7.60–7.52 (m, 3H), 6.82 (br s, 4H); Anal. calcd for C$_{15}$H$_{13}$N$_5$OS.0.25H$_2$O: C, 57.03; H, 4.30; N, 22.17. Found: C, 57.47; H, 4.04; N, 21.81.

EXAMPLE 58

6-[4-(phenylsulfonyl)phenyl]-1,3,5-triazine-2,4-diamine 4-(Phenylsulfonyl)benzonitrile (*J. Org. Chem.* 1989, 54, 4691) was processed as in Example 1, to provide the title compound.

mp>250° C.; MS (DCI/NH$_3$) m/e 328 (M+H)$^+$; $^1$H NMR (300 MHz, DMSO-d$_6$) δ 8.41 (d, 2H), 8.08 (d, 2H), 7.96 (d, 2H), 7.71–7.60 (m, 3H), 6.92 (br s, 4H); Anal. calcd for C$_{15}$H$_{13}$N$_5$O$_2$S.0.25H$_2$O: C, 54.28; H, 4.10; N, 21.10. Found: C, 54.28; H, 3.92; N, 20.82.

EXAMPLE 59

E/Z-[4-(4,6-diamino-1,3,5-triazine-2-yl)phenyl]phenylmethanone,oxime

A mixture of Example 11 (300 mg, 1.03 mmol) and hydroxylamine hydrochloride (70 mg, 1.0 mmol) in 1:1 ethanol/pyridine (10 mL) was heated at reflux for 3 hours, stirred overnight at room temperature, treated with water, and filtered. The precipitate was rinsed with water and dried to provide the title compound.

mp 97–107° C.; MS (DCI/NH$_3$) m/e 307 (M+H)$^+$; $^1$H NMR (300 MHz, DMSO-d$_6$) δ 11.42 (s, 0.5H), 11.41 (s, 0.5H), 8.35 (d, 1H), 8.2 (d, 1H), 7.3–7.5 (m, 7H), 6.8 (br s, 4H); Anal. calcd for C$_{16}$H$_{14}$N$_6$O.CH$_3$CH$_2$OH: C, 61.35; H, 5.72; N, 23.84. Found: C, 61.67; H, 5.29; N, 23.37.

EXAMPLE 60

6-pyrazinyl-1,3,5-triazine-2,4-diamine

Pyrazinecarbonitrile was processed as in Example 1 to provide the title compound.

mp>250° C.; MS (DCI/NH$_3$) m/e 190 (M+H)$^+$; $^1$H NMR (300 MHz, DMSO-d$_6$) δ 6.9 (br s, 2H), 7.1 (br s, 2H), 8.75–8.8 (m, 2H), 9.3 (s, 1H); Anal. calcd for C$_7$H$_7$N$_7$: C, 44.44; H, 3.72; N, 51.82. Found: C, 44.40; H, 3.62; N, 51.79.

EXAMPLE 61

2,4-diamino-6-[(4-phenylethenyl)phenyl]-1,3,5-triazine

EXAMPLE 61A

A solution of benzyltriphenylphosphonium chloride (22.8 g, 58 mmol) in THF (100 mL) at room temperature was treated with lithium hexamethyldisilazide (1M in toluene, 53 mL, 53 mmol), heated to reflux for 15 minutes, cooled to room temperature, treated with 4-cyanobenzaldehyde (7 g, 53 mmol) in THF (40 mL), stirred overnight at room temperature, acidified with 10% HCl, and filtered. The filtrate was extracted with ethyl acetate, dried (MgSO$_4$), and concentrated. The residue was dissolved in hot ethyl acetate and filtered through a plug of silica gel to provide the designated compound.

EXAMPLE 61B

Example 61A was processed as in Example 1 to provide the title compound.

mp 216–217° C.; MS (DCI/NH$_3$) m/e 290 (M+H)$^+$; $^1$H NMR (300 MHz, DMSO-d$_6$) δ 8.25 (d, 2H), 7.75 (d, 2H), 7.65 (d, 2H), 7.2–7.4 (m, 5H), 6.75 (br s, 4H); Anal. calcd for C$_{17}$H$_{15}$N$_5$.0.5CH$_3$CO$_2$CH$_2$CH$_3$: C, 68.45; H, 5.74; N, 21.00. Found: C, 68.50; H, 5.49; N, 21.43.

EXAMPLE 62

2,4-diamino-6-[(4-(2-nitrophenyl)ethenyl)phenyl]-1,3,5-triazine

4-Nitrobenzyltriphenylphosphonium bromide was processed as in Examples 61A and 61B to provide the title compound.

mp>250° C.; MS (DCI/NH$_3$) m/e 335 (M+H)$^+$; $^1$H NMR (300 MHz, DMSO-d$_6$) δ 8.25 (t, 4H), 7.9 (d, 2H), 7.8 (d, 2H), 7.6 (m, 2H), 6.8 (br s, 4H); Anal. calcd for C$_{17}$H$_{14}$N$_6$O$_2$: C, 61.07; H, 4.22; N, 25.14. Found: C, 60.78; H, 4.12; N, 24.89.

EXAMPLE 63

6-[1,1'-biphenyl]-4-yl-N,N'-dimethyl-1,3,5-triazine-2,4-diamine

EXAMPLE 63A 2-1,1'-biphenyl]-4-yl-4,6-dichloro-1,3,5-triazine

A mixture of 4-phenyl-phenyl magnesium bromide (prepared from 4-bromobiphenyl (7.75 g, 33 mmol) and magnesium turnings (0.83 g, 35 mmol) in 40 mL ether) and cyanuric chloride (4.00 g, 21.7 mmol) in benzene (90 mL) was stirred at 0° C. for 90 minutes. The reaction was evaporated to dryness, and the residue was flash chromatographed on silica gel with 50% hexanes/methylene chloride to provide the desired compound (2.80 g, 43%).

MS (DCI/NH$_3$) m/e 301 (M+H)$^+$.

EXAMPLE 63B 6-1,1'-biphenyl]-4-yl-N,N'-dimethyl-1,3,5-triazine-2,4-diamine

A mixture of Example 63A (0.52 g, 1.72 mmol) and N-methylamine (30 mmol) in tetrahydrofuran (25 mL) was stirred at ambient temperature for 72 hours. The reaction was reduced in volume and diluted with water. The precipitate was collected, rinsed with water and ether, and dried. Purification by reverse phase HPLC provided the desired compound.

mp 198–200° C.; MS (DCI/NH$_3$) m/e 292 (M+H)$^+$; $^1$H NMR (300 MHz, DMSO-d$_6$) δ 8.37 (m, 2H), 7.74 (m, 4H), 7.51 (m, 2H), 7.39 (m, 1H) 7.22 (bdm, 2H), 2.82 (m, 6H); Anal. calcd for C$_{17}$H$_{17}$N$_5$.0.25H$_2$O: C, 69.01; H, 5.96; N, 23.67. Found: C, 69.37; H, 5.85; N, 23.63.

EXAMPLE 64

6-[1,1'-biphenyl]-4-yl-N-methyl-1,3,5-triazine-2,4-diamine

EXAMPLE 64A

4-[1,1'-biphenyl]-4-yl-6-chloro-1,3,5-triazin-2-amine

A mixture of 2-[1,1'-biphenyl]-4-yl-4,6-dichloro-1,3,5-triazine (Example 63A) (0.804 g, 2.67 mmol) in 40 mL ether and concentrated ammonium hydroxide (2 mL, 30 mmol) in tetrahydrofuran (30 mL) was stirred at 0° C. for 60 minutes and at ambient temperature for 20 minutes. The reaction was reduced in volume, diluted with water, and the precipitate was collected, rinsed with water and ether, and dried to provide the desired compound (0.090 g, 12%).

MS (DCI/NH$_3$) m/e 282 (M+H)$^+$.

EXAMPLE 64B

6-[1,1'-biphenyl]-4-yl-N-methyl-1,3,5-triazine-2,4-diamine

Example 64A (0.090 g, 0.32 mmol) an d N-methylamine (6 mmol) in tetrahydrofuran (9 mL) was stirred at ambient temperature for 24 hours. The reaction was reduced in volume and diluted with water. The precipitate was collected, rinsed with water and ether, and dried to provide the desired compound (0.062 g, 70%).

mp 237–238° C.; MS (DCI/NH$_3$) m/e 278 (M+H)$^+$; $^1$H NMR (300 MHz, DMSO-d$_6$) δ 8.39 (d, 1H), 8.32 (d, 1H), 7.77 (m, 4H), 7.51 (t, 2H), 7.41 (m, 1H), 7.25 (q, 2H), 6.79 (bds, 2H), 2.79 (d, 3H); Anal. calcd for C$_{16}$H$_{15}$N$_5$.0.5C$_4$H$_8$O$_2$: C, 67.27; H, 5.96; N, 21.79. Found: C, 67.20; H, 5.71; N, 22.05.

EXAMPLE 65

6-(bicyclo[2.2.1]hept-2-yl)-1,3,5-triazine-2,4-diamine

EXAMPLE 65A

6-(bicyclo[2.2.1]hept-2-en-5-yl)-1,3,5-triazine-2,4-diamine

Bicyclo[2.2.1]hept-2-ene-5-carbonitrile was processed as in Example 1 to provide the desired compound.

MS (DCI/NH$_3$) m/e 204 (M+H)$^+$

EXAMPLE 65B

6-(bicyclo[2.2.1]hept-2-yl)-1,3,5-triazine-2,4-diamine

A solution of Example 65A in methanol was reduced with hydrogen gas and palladium on charcoal, filtered, and evaporated to provide the desired compound.

mp 216–217° C.; MS (DCI/NH$_3$) m/e 206 (M+H)$^+$; $^1$H NMR (300 MHz, DMSO-d$_6$) δ 6.52 (bds, 4H), 2.83 (m, 1H), 2.39 (m, 1H), 2.21 (m, 1H), 2.04 (m, 1H), 1.91 (m, 1H), 1.6–1.2 (m, 5H), 6.52 (m, 1H); Anal. calcd for C$_{10}$H$_{15}$N$_5$: C; 58.52, H; 7.37, N; 34.12. Found: C; 58.59, H; 7.40, N; 34.00.

EXAMPLE 66

6-[1,1'-biphenyl]-4-yl-N,N'-diethyl-1,3,5-triazine-2,4-diamine

A mixture of 2,4-di-N-ethylamino-6-chloro-1,3,5-triazine (0.55 g, 2.7 mmol) and tetrakis(triphenylphosphine) palladium (0.19 g, 0.16 mmol) in dry, degassed dimethylacetamide (45 mL) was heated to 100° C., treated sequentially with 4-(phenyl)phenyl boronic acid (Yabroff et al., *Journal of the American Chemical Society*, Volume 56, 1934, pp.1850–1856) (0.80 g, 4.0 mmol) in absolute ethanol (15 mL) and saturated aqueous sodium bicarbonate (30 mL), and the reaction mixture was maintained at 100° C. for 3 days. The reaction mixture was cooled to room temperature and diluted with ethyl acetate. The organic layer was washed with brine, dried (MgSO$_4$), concentrated, and vacuum dried. The residue was recrystallized from 2:1 dioxane/ethanol to provide 0.15 g (17%) of the desired compound as a white solid.

mp 183–184° C.; MS (DCI/NH$_3$) m/e 320 (M+H)$^+$; $^1$H NMR (300 MHz, DMSO-d$_6$) δ 8.36 (m, 2H), 7.78 (d, 2H), 7.73 (d, 2H), 7.49 (m, 2H), 7.38 (m, 1H), 7.28 (m, 2H), 3.40 (m, 4H), 1.16 (m, 6H); Anal. calcd for C$_{19}$H$_{21}$N$_5$.0.2C$_4$H$_8$O$_2$: C, 70.91; H, 6.55; N, 8.28. Found: C, 71.21; H, 6.50; N, 21.13.

EXAMPLE 67

6-(2'-nitro[1,1'-biphenyl]-4-yl)-1,3,5-triazine-2,4-diamine

4-Cyano-2'-nitrobiphenyl was processed as in Example 1 to provide the desired compound.

mp>250° C.; $^1$H NMR (300 MHz, DMSO-d$_6$) δ 8.3 (d, 2H, J=9 Hz), 8.05 (dd, 1H), 7.8 (m, 1H), 7.6–7.7 (m, 2H), 7.45 (d, 2H), 6.8 (br s, 4H); MS (DCI/NH$_3$) m/e 309 (M+H)$^+$; Anal. calcd for C$_{15}$H$_{12}$N$_6$O$_2$: C, 58.44; H, 3.92; N, 27.26. Found: C, 58.46; H, 3.99; N, 27.15.

EXAMPLE 68

6-(6-methyl-3-pyridinyl)-1,3,5-triazine-2,4-diamine

6-Methylnicotinonitrile was processed as in Example 1 to provide the desired compound.

mp>260° C.; MS (DCI/NH$_3$) m/e 203 (M+H)$^+$; $^1$H NMR (300 MHz, DMSO-d$_6$) δ 9.23 (d, 1H), 8.39 (dd, 1H, J=11), 7.38 (d, 1H), 6.81 (br s, 4H), 2.56 (s, 3H); Anal. calcd for C$_9$H$_{10}$N$_6$: C, 53.45; H. 4.98; N, 41.55. Found: C, 53.46; H, 4.94; N, 41.84.

EXAMPLE 69

6-(6-chloro-3-pyridinyl)-1,3,5-triazine-2,4-diamine

Methyl 6-chloronicotinate and imidodicarbonimidic diamide (2B) was processed as in Example 2C to provide the desired compound.

mp>260° C.; MS (DCI/NH$_3$) m/e 223, 225 (M+H)$^-$; $^1$H NMR (300 MHz, DMSO-d$_6$) δ 9.17 (d, 1H), 8.46 (dd, 1H, J=11), 7.62 (d, 1H), 6.91 (br s, 4H); Anal. calcd for C$_8$H$_7$ClN$_6$: C, 43.15; H, 3.16; N, 37.74. Found: C, 43.05; H, 3.08; N, 37.50.

EXAMPLE 70

6-(5-bromo-3-pyridinyl)-1,3,5-triazine-2,4-diamine

5-Bromonicotinonitrile was processed as in Example 1 to provide the desired compound.

mp>260° C.; MS (DCI/NH$_3$) m/e 267 (M+H)$^+$; $^1$H NMR (300 MHz, DMSO-d$_6$) δ 9.3 (d, 1H), 8.82 (d, 1H, J=3 Hz), 8.62–8.64 (m, 1H), 6.8–7.1 (brs, 1H); Anal. calcd for C$_8$H$_7$BrN$_6$: C, 35.98; H, 2.64; N, 31.47. Found: C, 35.89; H, 2.53; N, 31.22.

EXAMPLE 71

6-(2,3-dihydro-2,2,3,3-tetrafluoro-1,4-benzodioxin-6-yl)-1,3,5-triazine-2,4-diamine 6-Cyano-2,3-dihydro-2,2,3,3-tetrafluoro-1,4-benzodioxane was processed as in Example 1 to provide the desired compound.

mp 176–179° C.; MS (DCI/NH$_3$) m/e 275 (M+H)$^+$; $^1$H NMR (300 MHz, DMSO-d$_6$) δ 7.98 (d, 1H), 7.71 (d, 1H), 7.17 (dd, 1H), 7.16 (br s, 2H), 6.95 (br s, 2H), 3.85 (s, 3H); Anal. calcd for C$_{11}$H$_7$F$_4$N$_5$O$_2$: C; 41.65, H; 2.22, N; 22.08. Found: C; 41.55, H; 2.10, N; 22.09.

EXAMPLE 72

6-[4-[(4-chlorophenyl)methoxy]phenyl]-1,3,5-triazine-2,4-diamine

4-[(4-Chlorophenyl)methoxy]benzonitrile was processed as in Example 1 to provide the desired compound.

mp 246–248° C.; MS (DCI/NH$_3$) m/e 342 (M+H)$^+$; $^1$H NMR (300 MHz, DMSO-d$_6$) δ 7.45 (s, 4H), 7.25 (d, 2H), 6.9 (d, 2H), 6.6 (br s, 4H), 5.05 (s, 2H), 3.55 (s, 2H); Anal. calcd for C$_{17}$H$_{16}$ClN$_5$O: C, 59.74; H, 4.72; N, 20.49. Found: C, 59.64; H, 4.64; N, 20.49.

EXAMPLE 73

6-[4-(1-piperidinylsulfonyl)phenyl]-1,3,5-triazine-2,4-diamine

EXAMPLE 73A

1-[(4-cyanophenyl)sulfonyl]piperidine

A mixture of 4-cyanobenzenesulfonyl chloride (0.51 g, 2.5 mmol) and piperidine (0.60 mL, 517 mg, 6.04 mmol) in 10 mL methylene chloride was stirred overnight at ambient temperature. The organic layer was washed successively with water, 5% HCl and brine, dried (Na$_2$SO$_4$) and concentrated. The resulting white solid (0.61 g, 96%) was used with no further purification.

EXAMPLE 73B

6-[4-(1-piperidinylsulfonyl)phenyl]-1,3,5-triazine-2,4-diamine

The product of Example 73A was processed as in Example 1 to provide the desired compound.

m.p.>260° C.; MS (DCI/NH$_3$) m/e 335 (M+H)$^+$; $^1$H NMR (300 MHz, DMSO-d$_6$) δ 8.43 (d, 2H), 7.84 (d, 2H), 6.90 (bds, 4H), 2.90–2.97 (m, 4H), 1.50–1.59 (m, 4H), 1.32–1.42 (m, 2H); Anal. calcd for C$_{14}$H$_{18}$N$_6$O$_2$S: C, 50.28; H, 5.42; N, 25.13. Found: C, 50.43; H, 5.32; N, 25.12.

EXAMPLE 74

6-(1-benzoyl-4-piperidinyl)-1,3,5-triazine-2,4-diamine

EXAMPLE 74A 1-benzoyl-4-piperidinecarbonitrile

A mixture of 1-benzoyl-4-piperidone (2.0 g, 9.8 mmol), tosylmethyl isocyanide (2.5 g, 12.8 mmol) and ethanol (1.0 mL, 17.1 mmol) in 30 mL DME was cooled in an ethanol/ice bath, and potassium tert-butoxide was added at such a rate to maintain the reaction temperature at <10° C. The cold bath was removed, and the reaction was allowed to stir overnight at room temperature. The solids were removed by filtration, rinsed with DME, and the filtrate was evaporated. The residue was dissolved in EtOAc, washed with water and brine, dried (MgSO$_4$), filtered through silica gel, and concentrated to give 2.14 g (66%) of a slightly yellow oil.

EXAMPLE 74B 6-(1-benzoyl-4-piperidinyl)-1,3,5-triazine-2,4-diamine

The product of Example 74A was processed as in Example 1 to provide the desired compound.

m.p. 246–248° C.; MS (DCI/NH$_3$) m/e 299 (M+H)$^+$; $^1$H NMR (300 MHz, DMSO-d$_6$) δ 7.43–7.49 (m, 3H), 7.33–7.39 (m, 2H), 6.58 (bds, 4H), 4.44–4.52 (bm, 1H), 3.55–3.67 (bm, 1H), 2.79–3.27 (bm, 2H), 1.53–1.94 (bm, 5H); Anal. calcd for C$_{15}$H$_{18}$N$_6$O: C, 60.38; H, 6.08; N, 28.16. Found: C, 60.09; H, 6.02; N, 28.29.

EXAMPLE 75

6-[1-(phenylmethyl)-4-piperidinyl]-1,3,5-triazine-2,4-diamine

N-Benzyl-4-piperidone was processed as in example 74A and 74B to provide the desired compound.

m.p.>260° C.; MS (DCI/NH$_3$) m/e 285 (M+H)$^+$; $^1$H NMR (300 MHz, DMSO-d$_6$) δ 7.19–7.32 (m, 5H), 6.50 (bds, 4H), 3.44 (s, 2H), 2.78–2.86 (m, 2H), 2.16–2.28 (m, 1H), 1.90–1.99 (m, 2H), 1.63–1.76 (m, 4H); Anal. calcd for C$_{15}$H$_{20}$N$_6$.H$_2$O: C, 59.58; H, 7.33; N, 27.79. Found: C, 60.06; H, 7.19; N, 27.94.

EXAMPLE 76

N,N'-diacetyl-6-[4-(phenylsulfonyl)phenyl]-1,3,5-triazine-2,4-diamine

6-[4-(phenylsulfonyl)phenyl]1,3,5-triazine-2,4-diamine (Example 58) was processed as in Example 33B to provide the desired compound.

mp>260° C.; MS (DCI/NH$_3$) m/e 412 (M+H)$^+$; $^1$H NMR (300 MHz, DMSO-d$_6$) δ 8.52 (d, 2H, J=8 Hz), 8.18 (d, 2H, J=8 Hz), 8.01 (m, 2H), 7.73 (m, 1H), 7.68 (m, 2H), 2.37 (s, 6H); Anal. calcd for C$_{19}$H$_{17}$N$_5$O$_4$: C, 55.47; H, 4.16; N, 17.02. Found: C, 55.47; H, 4.19; N, 17.11.

EXAMPLE 77

N-acetyl-6-[4-(phenylsulfonyl)phenyl]-1,3,5-triazine-2,4-diamine

6-[4-(phenylsulfonyl)phenyl]1,3,5-triazine-2,4-diamine (Example 58) was processed as in Example 34 to provide the desired compound.

mp>260° C.; MS (DCI/NH$_3$) m/e 370 (M+H)$^+$; $^1$H NMR (300 MHz, CF$_3$CO$_2$D) δ 8.51 (d, 2H), 8.27 (d, 2H), 8.06 (d, 2H), 7.78 (t, 1H), 7.68 (t, 2H), 2.56 (s, 3H); Anal. calcd for C$_{17}$H$_{15}$N$_5$O$_3$.0.5H$_2$O: C, 53.96; H, 4.26; N, 18.51. Found: C, 53.75; H, 3.91; N, 18.83.

EXAMPLE 78

6-[2-(1-piperidinyl)phenyl)]-1,3,5-triazine-2,4-diamine 2-(1-piperidinyl)benzonitrile was processed as in Example 1 to provide the desired compound.

mp>250° C.; MS (DCI/NH$_3$) m/e 271 (M+H)$^+$; $^1$H NMR (300 MHz, DMSO-d$_6$) δ 7.27 (d, 2H), 6.93 (d, 2H), 6.89 (m, 1H), 6.63 (bds, 4H), 3.88 (m, 4H), 1.47 (bdm, 6H); Anal. calcd for C$_{14}$H$_{18}$N$_6$: C; 62.20, H; 6.71, N; 31.09. Found: C; 61.88, H; 6.36, N; 31.37.

What is claimed is:

1. A compound having Formula I,

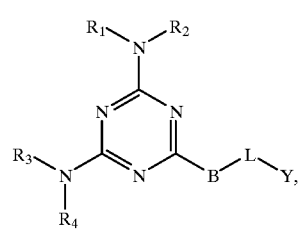

or pharmaceutically acceptable salts or prodrugs thereof, wherein $R_1$, $R_2$, $R_3$, and $R_4$ are independently selected from the group consisting of hydrogen, $C_1$–$C_{20}$-alkyl, and $C_1$–$C_{20}$-alkanoyl; or $R_1$ and $R_2$ together with the nitrogen atom to which they are attached form a ring independently selected from the group consisting of morpholine, piperidine, piperazine, and pyrrolidine; or $R_3$ and $R_4$ together with the nitrogen atom to which they are attached form a ring independently selected from the group consisting of morpholine, piperidine, piperazine, and pyrrolidine;

B is selected from the group consisting of phenyl, $C_3$–$C_{10}$-cycloalkyl, $C_4$–$C_{10}$-cycloalkenyl, azetidinyl, pyrrolidinyl, piperidinyl, pyrrolyl, oxazolyl, isoxazolyl, thiazolyl, isothiazolyl, furanyl, thienyl, pyridyl, pyridazinyl, pyrimidinyl, and pyrazinyl;

Y is selected from the group consisting of phenyl, $C_3$–$C_{10}$-cycloalkyl, $C_4$–$C_{10}$-cycloalkenyl, pyrrolidinyl, piperidinyl, morpholinyl, thiomorpholinyl, pyrrolyl, oxazolyl, isoxazolyl, thiazolyl, isothiazolyl, furanyl, thienyl, pyridyl, pyridazinyl, pyrimidinyl, and pyrazinyl;

wherein the groups defining B and Y are attached through substitutable carbon atoms or nitrogen atoms in the ring; and wherein the groups defining B and Y can be optionally substituted with 1–3 substituents independently selected from the group consisting of $C_1$–$C_{20}$-alkyl, $C_1$–$C_{20}$-alkoxy, amino, unsubstituted phenyl, azido, cyano, halo, $C_1$–$C_{20}$-haloalkyl, and nitro;

L is selected from the group consisting of a covalent bond, —C(=W)—, $C_1$–$C_{20}$-alkylene, —NR$_5$—, —NR$_6$C(X)NR$_7$—, $C_2$–$C_{20}$-alkynylene, $C_2$–$C_{20}$-alkenylene, —O—, —S(O)$_t$—, —NR$_6$C(X)—, —C(X)NR$_6$—, —NR$_6$SO$_2$NR$_7$—, —NR$_6$SO$_2$—, —SO$_2$NR$_6$—, —OC(R$_{100}$)(R$_{200}$)—, and —C(H)(R$_{300}$)—;

wherein each group defined by L is shown with its left end attached to B and its right end attached to Y $R_5$ is selected from the group consisting of hydrogen, $C_1$–$C_{20}$-alkyl, $C_1$–$C_{20}$-alkanoyl, and aryl-$C_1$–$C_{20}$-alkyl;

$R_6$ and $R_7$ are independently selected from the group consisting of hydrogen, $C_1$–$C_{20}$-alkyl, and aryl-$C_1$–$C_{20}$-alkyl;

$R_{100}$ and $R_{200}$ are selected from the group consisting of hydrogen, $C_1$–$C_{20}$-alkyl, and $C_1$–$C_{20}$-alkanoyl;

$R_{300}$ is selected from the group consisting of hydroxy and phenyl;

W is selected from the group consisting of O, S, and (=N—O—R$_6$);

X is selected from the group consisting of O and S; and t is 0–2;

all of the foregoing with the proviso that the following combinations are excluded therefrom:

one of B or Y is phenyl or pyridyl, and the other is phenyl or pyridyl;

B is phenyl; Y is cycloalkyl; and L is —O—; and $R_1$, $R_2$, $R_3$, and $R_4$ are hydrogen; B is $C_3$-cycloalkyl; Y is phenyl; and L is a covalent bond.

2. A compound according to claim 1 wherein B is phenyl.

3. A compound according to claim 1 wherein B is azetidinyl.

4. A compound according to claim 1 wherein B is piperidinyl.

5. A compound according to claim 1 wherein B is $C_4$-cycloalkyl.

6. A compound according to claim 1 wherein B is $C_6$-cycloalkyl.

7. A compound according to claim 1 wherein B is furanyl.

8. A compound according to claim 1 wherein B is thienyl.

9. A compound according to claim 1 wherein B is thiazolyl.

10. A compound according to claim 1 wherein $R_1$, $R_2$, $R_3$, and $R_4$ are hydrogen; B is $C_6$-cycloalkyl; Y is phenyl; and L is a covalent bond.

11. A compound selected from the group consisting of

6-[1-(diphenylmethyl)-3-azetidinyl]-1,3,5-triazine-2,4-diamine, 6-(1-phenyl-4-piperidinyl)-1,3,5-triazine-2,4-diamine, trans-6-(4-phenylcyclohexyl)-1,3,5-triazine-2,4-diamine, 6-[3-(1H-pyrrol-1-yl)phenyl]-1,3,5-triazine-2,4-diamine, cis/trans-6-(3-phenylcyclobutyl)-1,3,5-triazine-2,4-diamine, 6-[4-(4-pentylcyclohexyl)phenyl]-1,3,5-triazine-2,4-diamine, N-cyclohexyl-N'-[4-(4,6-diamino-1,3,5-triazin-2-yl)phenyl]urea, 6-[4-(5-oxazolyl)phenyl]-1,3,5-triazine-2,4-diamine, 6-[1-([1,1'-biphenyl]-4-yl)-4-piperidinyl]-1,3,5-triazine-2,4-diamine, 6-(1-phenylcyclohexyl)-1,3,5-triazine-2,4-diamine, 6-[1-(4-methoxyphenyl)-4-piperidinyl]-1,3,5-triazine-2,4-diamine, 6-[2-[4-(trifluoromethyl)phenyl]-4-thiazolyl]-1,3,5-triazine-2,4-diamine, 6-[1-(4-methoxyphenyl)cyclohexyl]-1,3,5-triazine-2,4-diamine, 6-[4-(2-thienyl)phenyl]-1,3,5-triazine-2,4-diamine, 6-[4-(4-morpholinylsulfonyl)phenyl]-1,3,5-triazine-2,4-diamine, 6-(5-phenyl-2-furanyl)-1,3,5-triazine-2,4-diamine, 6-(5-phenyl-2-thienyl)-1,3,5-triazine-2,4-diamine, N,N'-[6-(4-phenylcyclohexyl)-1,3,5-triazin-2,4-diyl]bis[acetamide], N-[4-amino-6-(4-phenylcyclohexyl)-1,3,5-triazin-2-yl]acetamide, (+/−)-4-(4,6-diamino-1,3,5-triazine-2-yl)-α-phenylbenzenemethanol, 6-[4-(1-piperidinylsulfonyl)phenyl]-1,3,5-triazine-2,4-diamine, 6-(1-benzoyl-4-piperidinyl)-1,3,5-triazine-2,4-diamine, 6-[1-(phenylmethyl)-4-piperidinyl]-1,3,5-triazine-2,4-diamine, and 6-(2-piperidin-1-ylphenyl)-1,3,5-triazine-2,4-diamine.

12. A compound according to claim 11 which is trans-6-(4-phenylcyclohexyl)-1,3,5-triazine-2,4-diamine.

* * * * *